US008706255B2

(12) United States Patent
Phillips et al.

(10) Patent No.: US 8,706,255 B2
(45) Date of Patent: *Apr. 22, 2014

(54) HOLSTER FOR CHARGING PECTORALLY IMPLANTED MEDICAL DEVICES

(75) Inventors: William C. Phillips, Brooklyn Park, MN (US); Charles R. Lewis, Jr., Palo Alto, CA (US); Rajeev M. Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 500 days.

This patent is subject to a terminal disclaimer.

(21) Appl. No.: 13/046,455

(22) Filed: Mar. 11, 2011

(65) Prior Publication Data

US 2011/0166630 A1      Jul. 7, 2011

Related U.S. Application Data

(63) Continuation of application No. 11/741,038, filed on Apr. 27, 2007, now Pat. No. 7,925,357, which is a continuation-in-part of application No. 11/414,155, filed on Apr. 28, 2006, now Pat. No. 7,738,965.

(51) Int. Cl.
*A61N 1/378* (2006.01)

(52) U.S. Cl.
USPC ............................................................ 607/61

(58) Field of Classification Search
USPC ............................................................ 607/61
See application file for complete search history.

(56) References Cited

U.S. PATENT DOCUMENTS

| | | | |
|---|---|---|---|
| 3,888,260 A | 6/1975 | Fischell | |
| 3,942,535 A | 3/1976 | Schulman | |
| 4,041,955 A | 8/1977 | Kelly et al. | |
| 4,071,032 A | 1/1978 | Schulman | |
| 4,134,408 A | 1/1979 | Brownlee et al. | |
| 4,143,661 A | 3/1979 | LaForge et al. | |
| 4,186,749 A | 2/1980 | Fryer | |
| 4,903,874 A | 2/1990 | Shoemaker | |
| 4,964,553 A | 10/1990 | Glynn | |
| 5,089,017 A | 2/1992 | Young et al. | |
| 5,115,382 A | 5/1992 | Smith | |
| 5,279,292 A | 1/1994 | Baumann et al. | |
| 5,314,453 A | 5/1994 | Jeutter | |

(Continued)

FOREIGN PATENT DOCUMENTS

| | | |
|---|---|---|
| EP | 0499939 A1 | 2/1992 |
| EP | 0499939 B1 | 2/1992 |

(Continued)

OTHER PUBLICATIONS

Medtronic, Inc., "Implantable Neurostimulation Systems", 1998.

(Continued)

*Primary Examiner* — Luther Behringer

(74) *Attorney, Agent, or Firm* — Beth L. McMahon

(57) ABSTRACT

A system for recharging an implantable medical device. The system comprises a holster that may be donned in multiple respective configurations for charging implanted medical devices implanted at various locations within the patient's body. The system may further comprise a charging unit having an antenna on the patient's right side, a second configuration for charging a pectorally implanted medical device on the patient's left side, or a third configuration for use as a waist belt for charging a pectorally implanted medical device on either side of the patient.

31 Claims, 24 Drawing Sheets

(56) References Cited

U.S. PATENT DOCUMENTS

| | | | |
|---|---|---|---|
| 5,333,768 | A | 8/1994 | Krentz |
| 5,411,537 | A | 5/1995 | Munshi et al. |
| 5,431,318 | A | 7/1995 | Garcia |
| 5,527,348 | A | 6/1996 | Winkler et al. |
| 5,562,714 | A | 10/1996 | Grevious |
| 5,613,935 | A | 3/1997 | Jarvik |
| 5,623,735 | A * | 4/1997 | Perry .................................. 2/327 |
| 5,690,693 | A | 11/1997 | Wang et al. |
| 5,713,939 | A | 2/1998 | Nedungadi et al. |
| 5,733,313 | A | 3/1998 | Barreras, Sr. et al. |
| 5,741,306 | A | 4/1998 | Glegyak et al. |
| 5,861,019 | A | 1/1999 | Sun et al. |
| 5,884,198 | A | 3/1999 | Kese et al. |
| 5,915,609 | A | 6/1999 | Diakoulas |
| 5,991,665 | A | 11/1999 | Wang et al. |
| 6,067,474 | A | 5/2000 | Schulman et al. |
| 6,097,982 | A | 8/2000 | Glegyak et al. |
| 6,154,677 | A | 11/2000 | Leysieffer |
| 6,178,353 | B1 | 1/2001 | Griffith et al. |
| 6,272,382 | B1 | 8/2001 | Faltys et al. |
| 6,275,737 | B1 | 8/2001 | Mann |
| 6,280,461 | B1 | 8/2001 | Glegyak et al. |
| 6,308,101 | B1 | 10/2001 | Faltys et al. |
| 6,321,126 | B1 | 11/2001 | Kuzma |
| 6,324,430 | B1 | 11/2001 | Zarinetchi et al. |
| 6,327,504 | B1 | 12/2001 | Dolgin |
| 6,389,318 | B1 | 5/2002 | Zarinetchi |
| 6,393,325 | B1 | 5/2002 | Mann et al. |
| 6,478,820 | B1 | 11/2002 | Weiss |
| 6,505,077 | B1 | 1/2003 | Kast et al. |
| 6,516,227 | B1 | 2/2003 | Meadows et al. |
| 6,609,032 | B1 | 8/2003 | Woods et al. |
| 6,738,671 | B2 | 5/2004 | Christophersom et al. |
| 6,814,270 | B2 | 11/2004 | Mason |
| 6,922,176 | B2 | 7/2005 | Haller et al. |
| 6,924,619 | B2 | 8/2005 | Dvorak et al. |
| 2001/0002441 | A1 | 5/2001 | Boveja |
| 2002/0055763 | A1 | 5/2002 | Zarinetchi et al. |
| 2002/0058971 | A1 | 5/2002 | Zarinetchi |
| 2002/0087204 | A1 | 7/2002 | Kung et al. |
| 2002/0177884 | A1 | 11/2002 | Ahn et al. |
| 2003/0078634 | A1 | 4/2003 | Schulman et al. |
| 2003/0114899 | A1 | 6/2003 | Woods et al. |
| 2003/0120323 | A1 | 6/2003 | Meadows et al. |
| 2004/0140939 | A1 | 7/2004 | Haller et al. |
| 2005/0004619 | A1 | 1/2005 | Wahlstrand et al. |
| 2005/0075698 | A1 | 4/2005 | Phillips et al. |
| 2005/0075699 | A1 * | 4/2005 | Olson et al. ..................... 607/61 |
| 2005/0113887 | A1 | 5/2005 | Bauhahn et al. |
| 2005/0228462 | A1 | 10/2005 | Brighton et al. |
| 2005/0245971 | A1 | 11/2005 | Brockway et al. |
| 2005/0245996 | A1 | 11/2005 | Phillips et al. |
| 2006/0089683 | A1 | 4/2006 | Hagglof et al. |
| 2006/0135863 | A1 | 6/2006 | Birnbaum et al. |

FOREIGN PATENT DOCUMENTS

| | | |
|---|---|---|
| EP | 0811395 A2 | 12/1997 |
| EP | 0811395 A3 | 12/1997 |
| EP | 1048324 A2 | 11/2000 |
| EP | 1443592 A2 | 8/2004 |
| EP | 1443592 B1 | 8/2004 |
| GB | 2143135 A | 2/1985 |
| WO | 98/37926 A1 | 9/1998 |
| WO | 99/06108 A1 | 2/1999 |
| WO | 99/44684 A1 | 9/1999 |
| WO | 00/01442 A2 | 1/2000 |
| WO | 00/02212 A1 | 1/2000 |
| WO | 01/83029 A1 | 11/2001 |
| WO | 01/97908 A2 | 12/2001 |
| WO | 01/97908 A3 | 12/2001 |
| WO | 02/053226 A2 | 7/2002 |
| WO | 03/009652 A2 | 1/2003 |
| WO | 2005/037369 A1 | 4/2005 |
| WO | 2005/110540 A1 | 11/2005 |

OTHER PUBLICATIONS

Medtronic, Inc. "Mattrix Neurostimulation System", Brochure, 1995.

Sinha, Gunjan, "The Heart, Medicine & Health", Popular Science, p. 43, Feb. 2000.

Partial International Search Report dated Feb. 10, 2010.

* cited by examiner

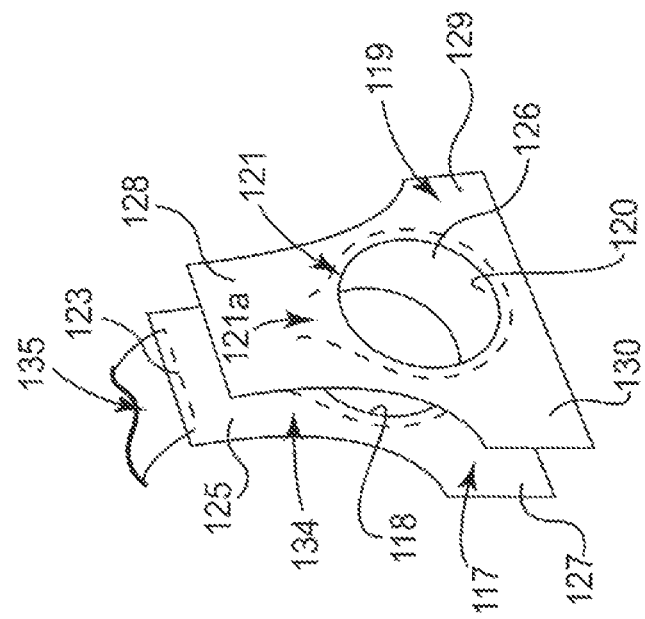
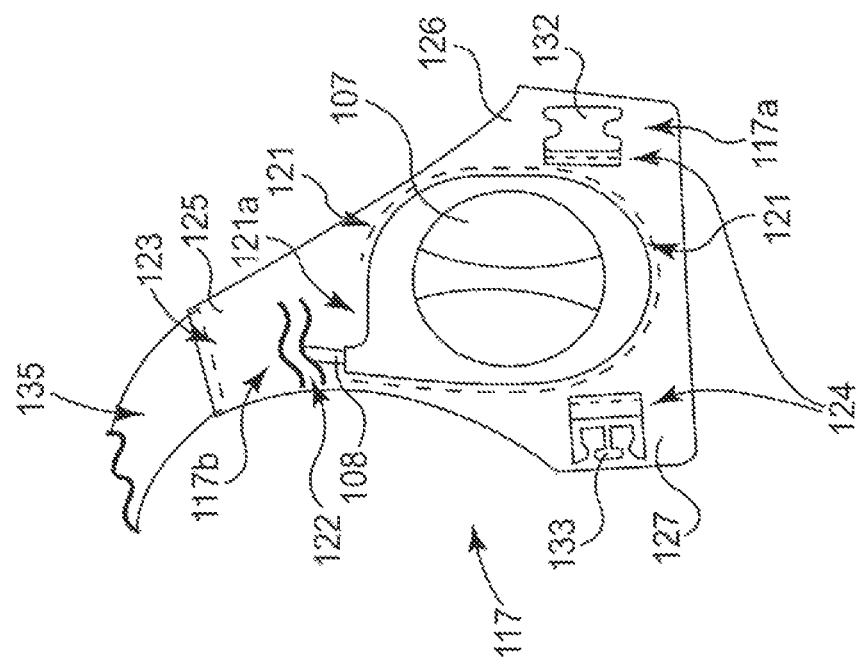

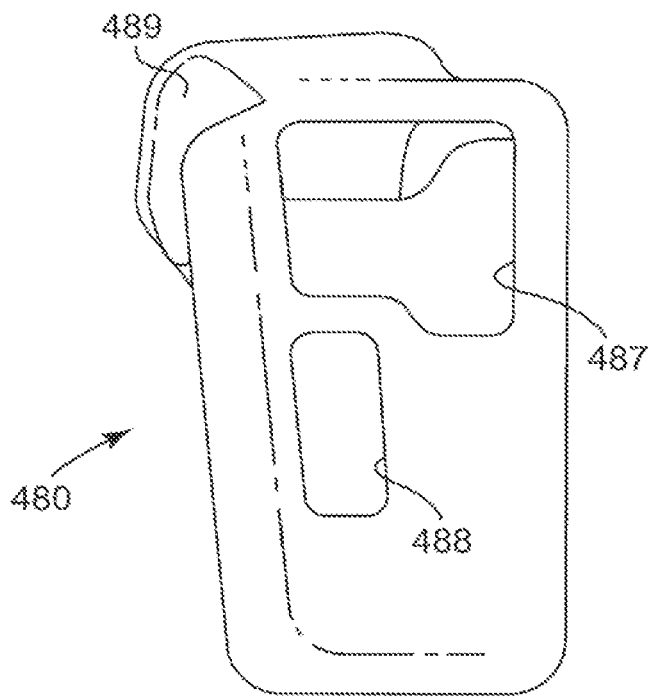
Fig. 30
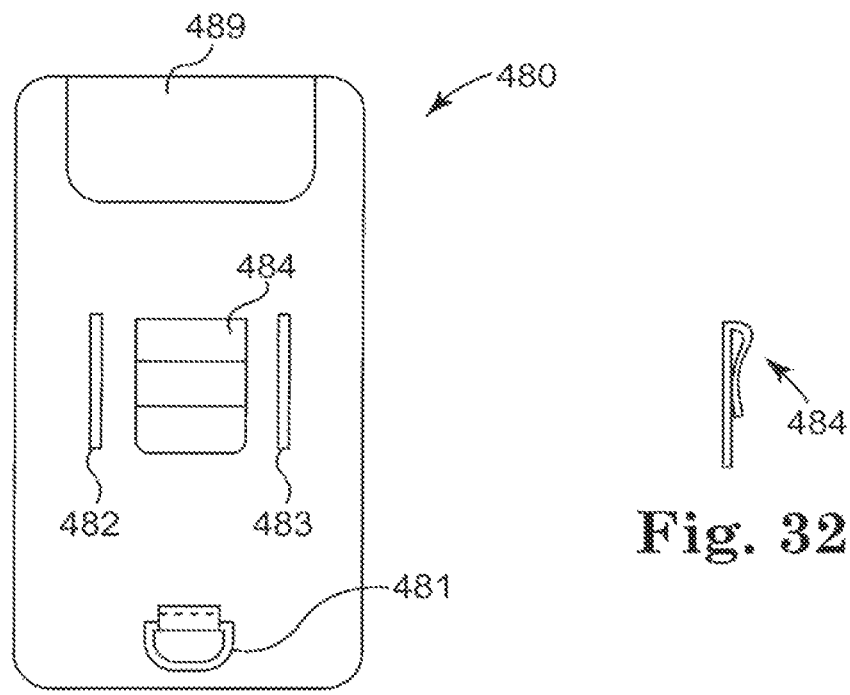
Fig. 31
Fig. 32

HOLSTER FOR CHARGING PECTORALLY IMPLANTED MEDICAL DEVICES

This application is a continuation of U.S. patent application Ser. No. 11/741,038 filed Apr. 27, 2007, now U.S. Pat. No. 7,925,357, which is a continuation-in-part application of U.S. patent application Ser. No. 11/414,155, filed Apr. 28, 2006, now U.S. Pat. No. 7,738,965, both of which are incorporated herein by reference in their entireties.

FIELD

The present disclosure relates to a holster for charging pectorally implanted medical devices.

BACKGROUND

Implantable medical devices for producing a therapeutic result in a patient are well known. An example of such an implantable medical device includes implantable neurostimulators used for the treatment of movement disorders such as Parkinson's Disease, essential tremor, and dystonia. Other examples of such implantable medical devices include implantable drug infusion pumps, implantable cardioverters, implantable cardiac pacemakers, implantable defibrillators, and cochlear implants. Of course, it is recognized that other implantable medical devices are envisioned that utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse, or providing an electrical cardiac stimulation pulse. This electrical power is derived from a power source.

Typically, a power source for an implantable medical device can take one of two forms. The first form utilizes an external power source that transcutaneously delivers energy via wires or radio frequency energy. Having electrical wires that perforate the skin is disadvantageous due, in part, to the risk of infection. Further, continuously coupling patients to an external power for therapy is, at least, a large inconvenience. The second form utilizes single cell batteries as the source of energy of the implantable medical device. This can be effective for low power applications, such as pacing devices. However, such single cell batteries usually do not supply the lasting power required to perform new therapies in newer implantable medical devices. In some cases, such as an implantable artificial heart, a single cell battery might last the patient only a few hours. In other, less extreme cases, a single cell unit might expel all or nearly all of its energy in less than a year. This is not desirable due to the need to explant and re-implant the implantable medical device or a portion of the device. One solution is for electrical power to be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin. Several systems and methods have been used for transcutaneously inductively recharging a rechargeable battery used in an implantable medical device.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger or recharger. The primary coil is driven with an alternating current. A current is induced in the secondary coil through inductive coupling. This current can then be used to power the implanted medical device or to charge or recharge an internal power source or a combination of the two.

For implanted medical devices, the efficiency at which energy is transcutaneously transferred may be crucial. First, the inductive coupling, while inductively inducing a current in the secondary coil, also has a tendency to heat surrounding components and tissue. The amount of heating of surrounding tissue, if excessive, can be deleterious. Since heating of surrounding tissue is limited, so also is the amount of energy transfer that can be accomplished per unit time. The higher the efficiency of energy transfer, the more energy can be transferred while at the same time limiting the heating of surrounding components and tissue. Second, it is desirable to limit the amount of time required to achieve a desired charge, or recharge, of an internal power source. While charging or recharging is occurring, the patient necessarily has an external encumbrance attached to his or her body. This attachment may impair the patient's mobility and limit the patient's comfort. The higher the efficiency of the energy transfer system, the faster the desired charging or recharging can be accomplished thus limiting any inconvenience to the patient. Third, the amount of charging or recharging can be limited by the amount of time required for charging or recharging. Since the patient is typically inconvenienced during such charging or recharging, there is a practical limit on the amount of time during which charging or recharging should occur. Hence, the size of the internal power source can be effectively limited by the amount of energy that can be transferred within the amount of charging time. The higher the efficiency of the energy transfer system, the greater amount of energy that can be transferred and, hence, the greater the practical size of the internal power source. This allows the use of implantable medical devices having higher power use requirements and providing greater therapeutic advantage to the patient and/or extends the time between charging effectively increasing patient comfort.

Implantable medical devices, external power sources, systems and methods have not always provided the best possible system or method for allowing the patient to be ambulatory during energy transfer and/or charging. Physical limitations related to the energy transfer and/or charging apparatus and methods as well as necessary efficiencies of operation can effectively limit the patient's ability to move around during such energy transfer and/or charging and can deleteriously affect patient comfort.

SUMMARY

One aspect of the current disclosure provides a system to transcutaneously charge a power supply of an implantable device. The system includes a charging unit, an antenna coupled to the charging unit and a strap. The strap comprises a shoulder strap portion adapted to be supported by a shoulder of the patient and a second strap portion adapted to encircle a portion of the patient. A cavity is carried by the strap and, in one example, is positionable to a location proximate the implantable device. The cavity is adapted to receive the antenna. In a particular example, the second strap portion may be adapted to receive the chest or waist of the patient. The shoulder strap portion may, in one instance, be removable. At least one of the shoulder strap portion and the second strap portion may be adjustable.

In another example, a system is provided that includes a charging unit, an antenna coupled to the charging unit, an implantable device adapted to receive energy from the charging unit, and a strap. The strap comprises a shoulder strap portion adapted to be supported by a shoulder of the patient. A cavity may be carried by the strap and may be positionable to a location proximate the implantable device. The cavity may be adapted to receive the antenna.

In yet a further example, a system is disclosed that comprises an implantable device adapted to be implanted in a patient. The system further includes a charging unit, an antenna coupled to charging unit, and a strap adapted to be supported by a portion of the patient's body. The strap comprises a cavity adapted to carry the antenna to allow the antenna to transcutaneously provide energy to the implantable device. In one particular embodiment, the cavity is positionable relative to the implantable device.

Other examples and aspects are described by the drawings and the accompanying description.

BRIEF DESCRIPTION OF THE DRAWINGS

FIG. 6 is a front view of an external antenna operatively connected to a rear panel of an antenna holder of the holster shown in FIG. 3;

FIG. 7 is a front perspective view of a rear panel and a front panel of an antenna holder of the holster shown in FIG. 3;

FIG. 30 is a front perspective view of the charging unit holder shown in FIG. 20;

FIG. 31 is a rear view of the charging unit holder shown in FIG. 30; and

FIG. 32 is a side view of a clip of the charging unit holder shown in FIG. 31.

DETAILED DESCRIPTION OF A PREFERRED EMBODIMENT

Figure 1:
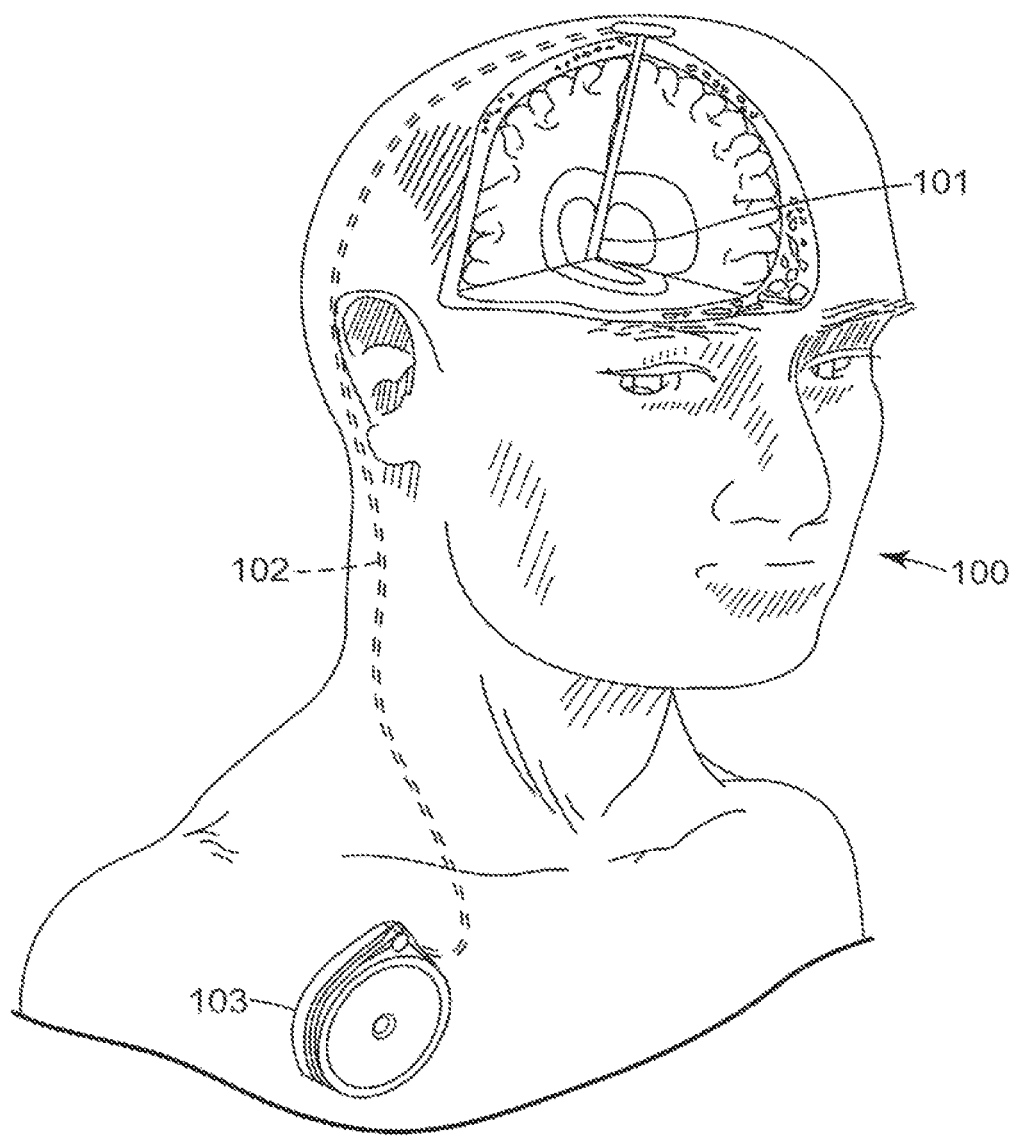
FIG. 1 illustrates an implantable medical device implanted in a patient.

A preferred embodiment holster for charging pectorally implanted medical devices constructed according to the principles of the present disclosure is designated by the numeral 115 in the drawings, another embodiment holster for charging pectorally implanted medical devices constructed according to the principles of the present disclosure is designated by the numeral 215 in the drawings, another embodiment holster for charging pectorally implanted medical devices constructed according to the principles of the present disclosure is designated by the numeral 315 in the drawings, and another embodiment holster for charging pectorally implanted medical devices constructed according to the principles of the present disclosure is designated by the numeral 415 in the drawings.

The holsters 115, 215, 315, and 415 may be used to charge any suitable pectorally implanted medical device. The term "charge" refers to any type of charge including, but not limited to, an initial charge and a recharge. The pectoral region is preferably proximate the pectoral muscles and is more preferably within a region of the body below the clavicle, above the xiphoid process of the sternum, and between the sternum and the axilla, which is a cavity beneath the junction of the arm and the torso. An example of a suitable pectorally implanted medical device for use with the present disclosure is disclosed in U.S. Patent Publication No. US 2005/0245996 A1, published Nov. 3, 2005, entitled Spacers for Use with Transcutaneous Energy Transfer System.

FIG. 1 shows a pectorally implanted medical device 103, for example a neurostimulator used for the treatment of a movement disorder such as Parkinson's Disease, essential tremor, and dystonia, implanted in the pectoral region of a patient 100. The pectorally implanted medical device 103 is typically implanted by a surgeon in a sterile surgical procedure performed under local, regional, or general anesthesia. During the sterile surgical procedure, a catheter 102 is typically implanted with the distal end position at a desired therapeutic delivery site 101 and the proximal end tunneled under the skin to the location where the pectorally implanted medical device 103 is to be implanted. The pectorally implanted medical device 103 is then implanted. Once the pectorally implanted medical device 103 is implanted into the patient 100, the incision can be sutured closed and pectorally implanted medical device 103 can begin operation. The pectorally implanted medical device 103 can be any suitable implantable medical device such as, but not limited to, implantable neurostimulators, implantable drug infusion pumps, implantable cardioverters, implantable cardiac pacemakers, implantable defibrillators, and cochlear implants.

The pectorally implanted medical device 103 includes a rechargeable power source that can be charged while the pectorally implanted medical device 103 is implanted in a patient through the use of an external charging device, which is a power source, comprising an external antenna 107 and a charging unit 109. The charging unit 109 may also be referred to as a recharger. The charging unit 109 contains the electronics necessary to drive a primary coil in the antenna 107 with an oscillating current in order to induce a current in a secondary coil in the pectorally implanted medical device 103 when the primary coil in the antenna 107 is placed in proximity of the secondary coil in the pectorally implanted medical device 103. The charging unit 109 is preferably operatively coupled to the primary coil in the antenna 107 by cable 108. Suitable charging units include without limitation those described in U.S. Patent Publication Nos. 2005/0113887; 2005/0075700; 2005/0075699; 2005/0075698; 2005/0075697; 2005/0075696; 2005/0075694; and 2005/0075693; all of which are incorporated herein by reference. It is also recognized that the charging unit 109 and the antenna 107 may be contained in a common housing rather than in separate housings.

The pectorally implanted medical device 103, when implanted, usually leaves an area of the patient's body that is not quite as flat as it was before implantation. That is, the pectorally implanted medical device 103 usually leaves a bulging area 106 proximate the surface of the patient's skin which bulges outward somewhat to accommodate the bulk of the pectorally implanted medical device 103. It is typically relatively easy for the patient, the medical professional, or another person to place the antenna 107 in the general area of the pectorally implanted medical device 103 and move the antenna 107 around until the antenna 107 is relatively centered with the bulging area 106. Once the antenna 107 is positioned in this manner, the antenna 107 can be secured to the patient's body.

Figure 2:
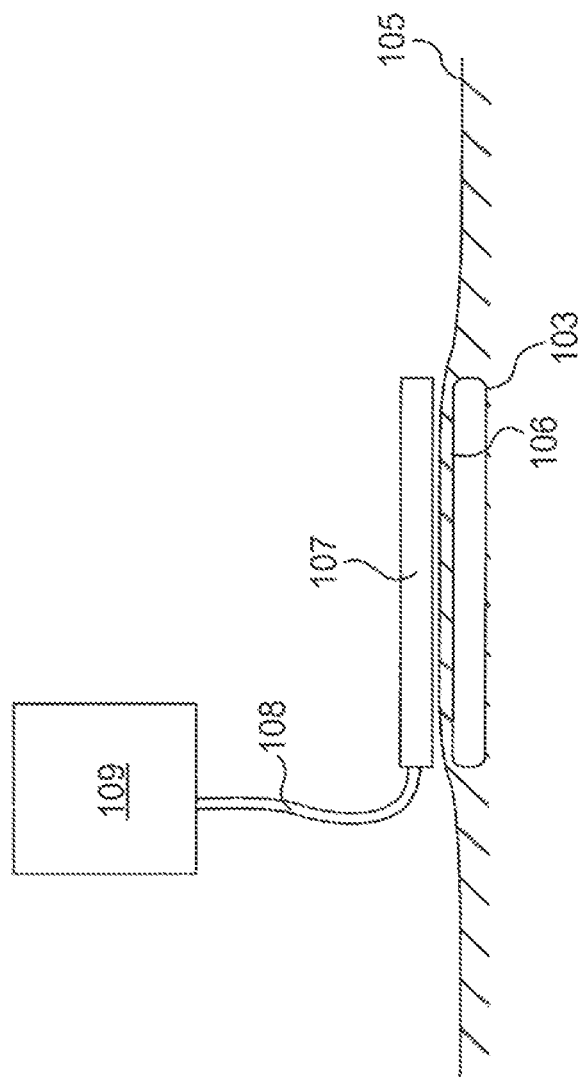
FIG. 2 is a schematic cross-sectional side view of an external antenna and an implanted medical device implanted in a patient.

As shown in FIG. 2, a schematic cross-sectional side view of an antenna 107 and a pectorally implanted medical device 103 implanted subcutaneously in the pectoral region of a patient, the pectorally implanted medical device 103 is implanted in a patient under cutaneous boundary 105 creating bulging area 106, an area of the patient's body in which the patient's skin is caused to bulge slightly due to the implantation of the pectorally implanted medical device 103. Bulging area 106 is an aid to locating the position of the secondary coil in the pectorally implanted medical device 103 and the antenna 107 can be positioned proximate the area where the pectorally implanted medical device 103 is implanted.

The antenna 107 is placed over the bulging area 106 as a power source to charge the pectorally implanted medical device 103. Depending upon the application and the pectorally implanted medical device 103, the pectorally implanted medical device 103 is generally implanted subcutaneously at depths of from 1 centimeter (0.4 inches) to 2.5 centimeters (1 inch) where there is sufficient tissue to support the implanted system. However, the locations of the implantation vary from patient to patient. The amount of bone and the amount of soft tissue between the bone and the cutaneous boundary 105 are factors that affect the actual depth of implant. The actual depth of implant as well as the amount of soft tissue at, and around, the implant site affect the size and shape of bulging area 106 at the implant site. Further, the location of the pectorally implanted medical device may vary in the patient due to any movement of the pectorally implanted medical device, especially if the pectorally implanted medical device is not sutured into place, any weight loss or gain, or any loss or gain of muscle mass.

This type of a transcutaneous energy transfer system can be utilized over extended periods of time, either to power the pectorally implanted medical device 103 over an extended period of time or to charge a replenishable power supply within the pectorally implanted medical device 103. Depending upon the capacity of the replenishable power supply and the efficiency of the energy transfer, the charging unit 109 and the antenna 107 can be utilized for hours. Further, over the extended period of time in which the charging unit 109 is utilized, antenna 107 is affixed to the patient's body. As the patient attempts to continue a normal routine, such as by making normal movement or by sleeping, during the energy transfer, it may be difficult to maintain the antenna 107 in a fixed position relative to the secondary coil in the pectorally implanted medical device 103. Movement of the antenna 107 with respect to the secondary coil can result in a change in mutual inductance, $L_{mutual}$, a change in impedance, and a change in the resonant frequency, $f_{resonate}$. Further, any change in spatial positioning of the energy transfer system with any external conductive object, any change in the characteristics of the antenna 107, such as by fractures in the magnetic core, for example, a change in the charge level of the rechargeable power source of the pectorally implanted medical device 103 or a change in the power level of the charging unit 109, all of which can result in a change of mutual inductance, $L_{mutual}$.

The pectoral region of the patient is typically not a flat surface so the antenna 107 may not sit completely flat against the patient's skin. This may be especially true as the patient moves and the pectoral region moves during such movement. Therefore, it is preferred that the holster 115, the holster 215, the holster 315, and the holster 415 be conformal and flexible in order to conform to the shape of the patient's pectoral region.

Figure 3:
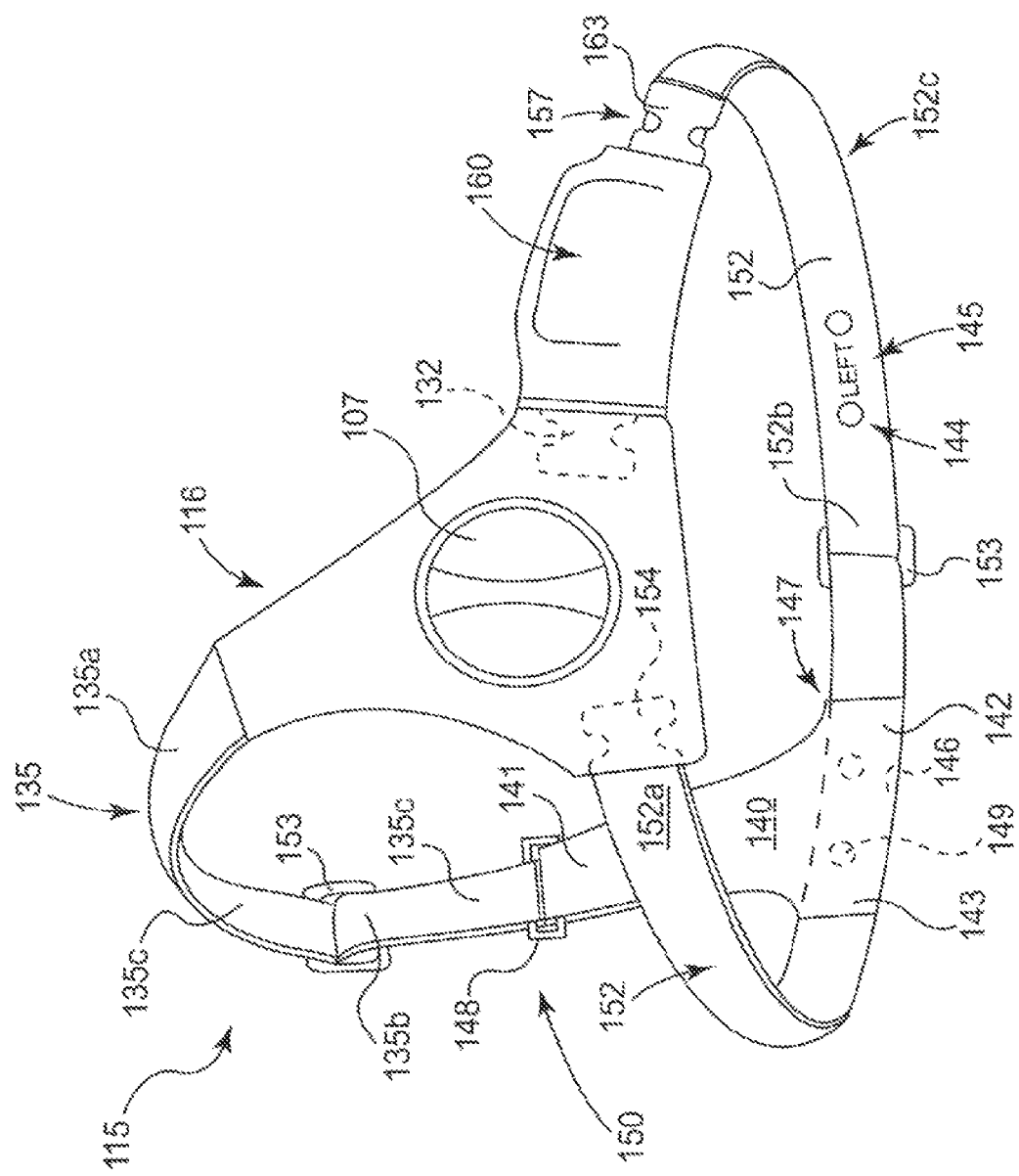
FIG. 3 is a front perspective view of a holster for charging a pectorally implanted medical device on a patient's right side.
Figure 4:
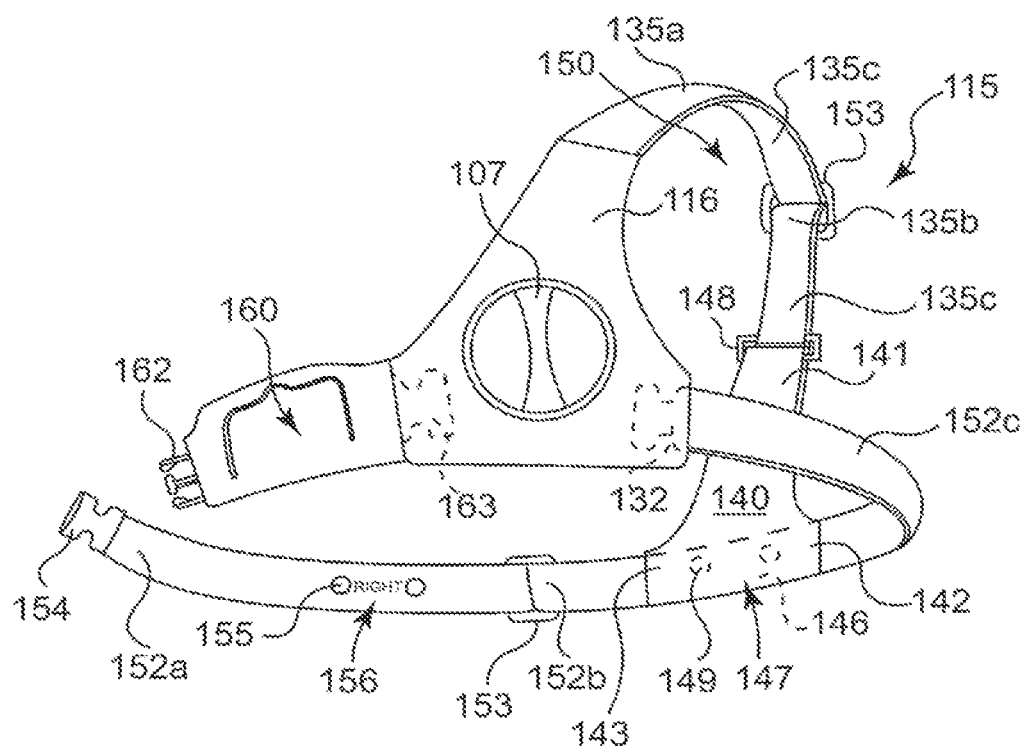
FIG. 4 is a front perspective view of the holster shown in FIG. 3 for charging a pectorally implanted medical device on a patient's left side.
Figure 8:
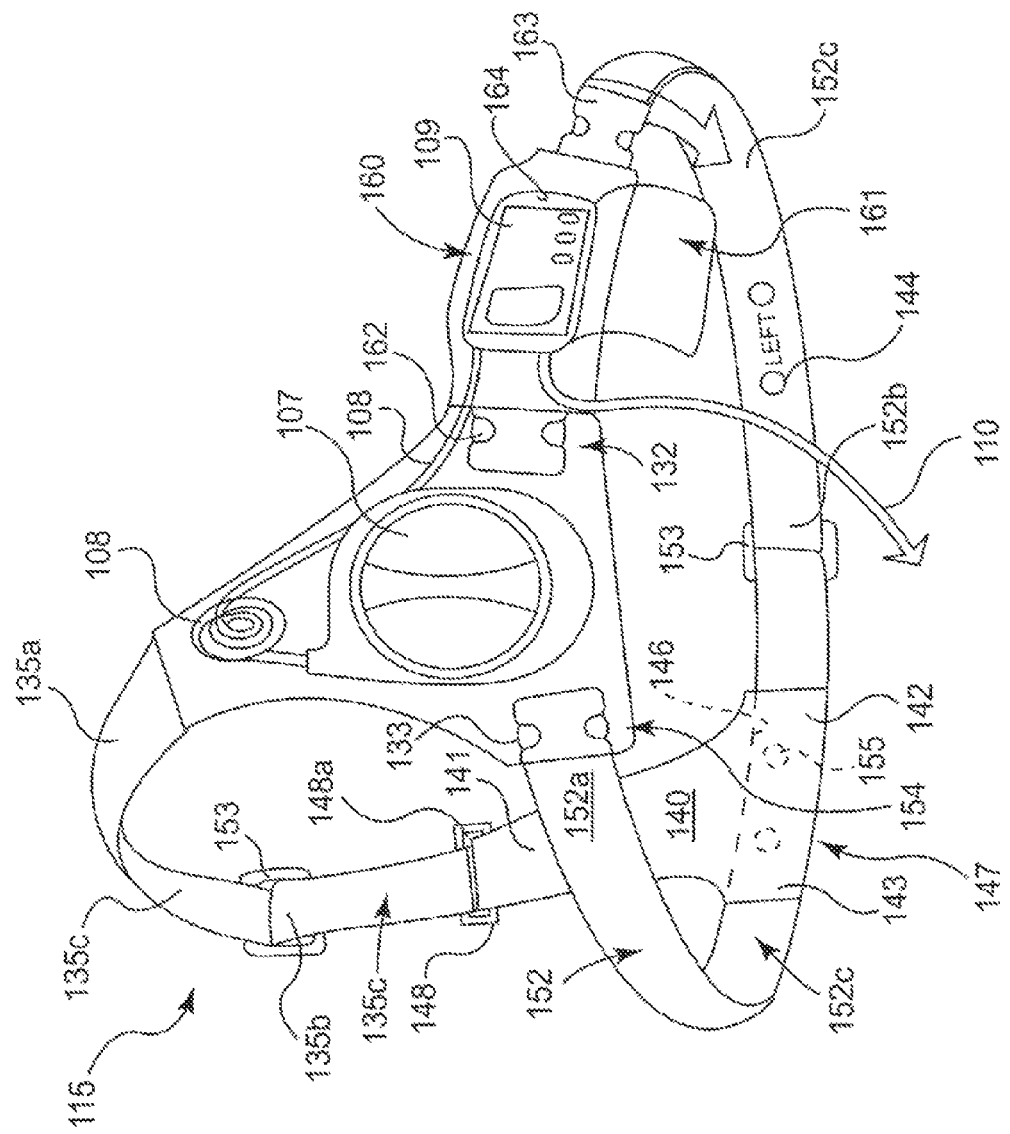
FIG. 8 is a front perspective view of the holster shown in FIG. 3 with a front panel of an antenna holder removed and an access panel of a rechargeable power source in an open position.

As shown in FIGS. 3, 4, and 8, the holster 115 includes an antenna holder 116, a shoulder strap 135, a chest strap 152, and a charging unit holder 160. The antenna holder 116 includes a first panel 117 and a second panel 119 forming a cavity 134 therebetween configured and arranged to house an antenna 107. The first panel 117 preferably includes a rectangular base portion 117a with a truncated triangular portion 117b having concave sides extending upward from the rectangular base portion 117a. The first panel 117 has a top portion 125 proximate the top of the truncated triangular portion 117b and a left portion 126 and a right portion 127 proximate opposing sides of the rectangular base portion 117a. The second panel 119 preferably also includes a rectangular base portion 119a with a truncated triangular portion 119b having concave sides extending upward from the rectangular base portion 119b. The second panel 119 has a top portion 128 proximate the top of the truncated triangular portion 119b and a left portion 129 and a right portion 130 proximate opposing sides of the rectangular base portion 119a. The first panel 117 is the inner layer proximate the patient's skin and the second panel 119 is the outer layer. The first panel 117 and the second panel 119 are approximately the same size and include corresponding circular openings 118 and 120, respectively, with the opening 120 preferably being slightly larger in diameter than the opening 118. The opening 118 allows the antenna 107 to contact the patient's skin, and the opening 120 provides access to the antenna 107.

Figure 16:
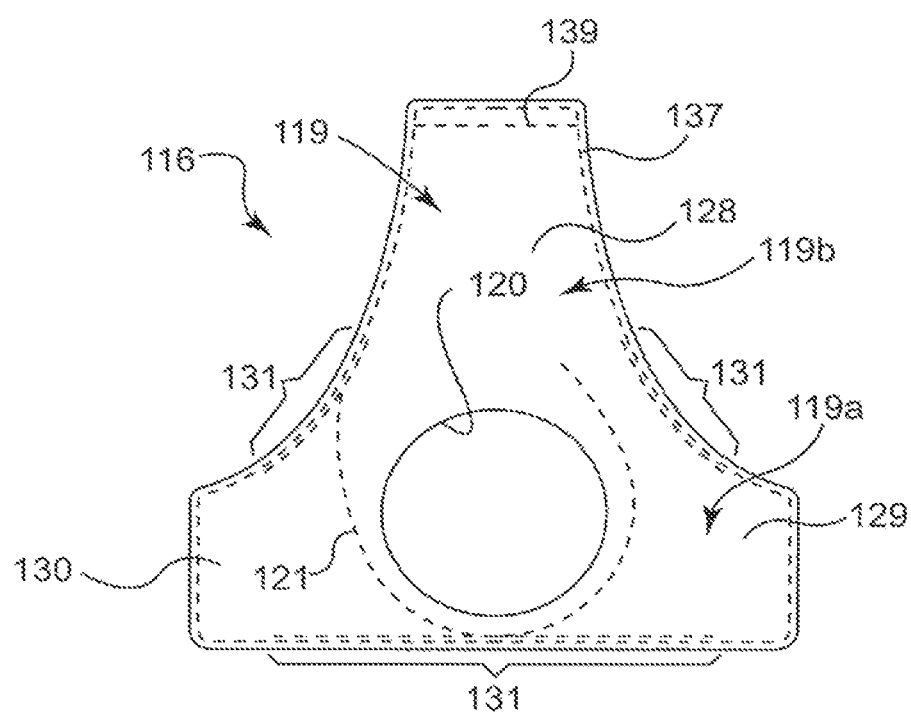
FIG. 16 is a front view of a front panel of the holster shown in FIG. 3.

Stitching is preferably used to connect the first panel 117 and the second panel 119 together and to hold the antenna 107 in place within the cavity 134. FIGS. 6, 7, and 16 show the preferred stitching patterns. Stitching 121 partially encircles openings 118 and 120 proximate the perimeter of the antenna 107 leaving a gap 121a proximate the top of the openings 118 and 120 to allow the cable 108 to extend upward therethrough as shown in FIG. 6. Stitching 121 holds the antenna 107 in place within the cavity 134 so that the antenna 107 is accessible through the openings 118 and 120. Stitching 122 may be used to secure the cable 108 to the first panel 177 in an upward orientation relative to the antenna holder 116. Stitching 131 is preferably used to secure the first panel 117 and the second panel 119 closed proximate the bottoms of the rectangular portions 117a and 119a and the sides of the truncated triangular portions 117b and 119b. A fastener (not shown) such as hook and loop may be connected to the outer surface of the top portion 125 and to the inner surface of the top portion 128 so that the top portions 125 and 128 are releasably connectable to allow access to the cavity 134. As shown in FIG. 16 for the second panel 119, stitching 137 may be used to finish the edge of the second panel 119 and stitching 137 and 139 may be used to secure the fastener to the top portion 128 of the second panel 119. The stitching patterns shown in FIG. 16 for the second panel 119 may also be used for the first panel 117. In addition, stitching 124 connects buckle portions 132 and 133 to the left portion 126 and the right portion 127, respectively, of the first panel 117 and stitching 123 connects a first end 135a of a shoulder strap 135 to the top portion 125 of the first panel 117. Because the left portions 126 and 129 and the right portions 127 and 120 are not stitched together, the buckle portions 132 and 133 are accessible between the first and second panels 117 and 119.

Figure 14:
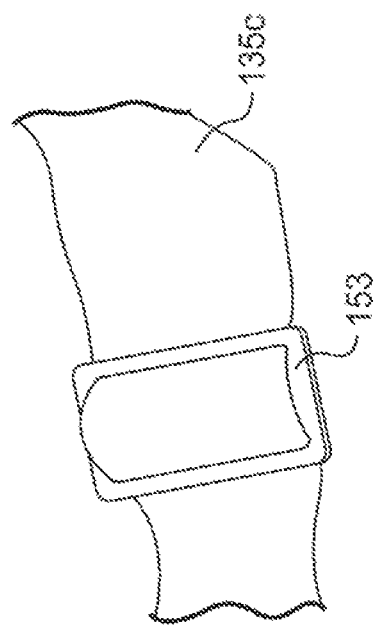
FIG. 14 is a front perspective view of the connector shown in FIG. 13 operatively connected to a strap.
Figure 13:
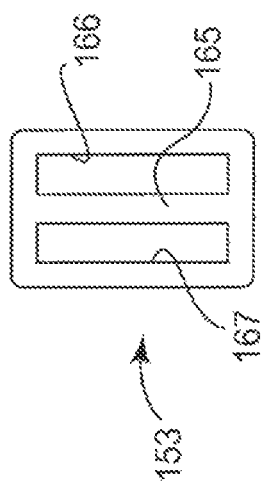
FIG. 13 is a front view of a connector.
Figure 15:
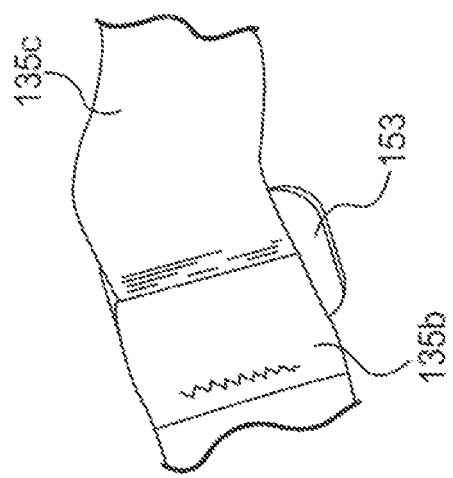
FIG. 15 is a rear perspective view of the connector shown in FIG. 13 operatively connected to a strap.

The shoulder strap 135 includes the first end 135a, a second end 135b, and an intermediate portion 135c between the first end 135a and the second end 135b. The first end 135a is connected to the top portion 125 of the first panel 117, and the second end 135b is connected to a middle bar portion 165 of an adjuster 153. The intermediate portion 135c of the shoulder strap 135 is routed through slots 166 and 167 of the adjuster 153 and through a slot 148a of a connector 148, which connects the intermediate portion 135c to a junction 140. FIGS. 13-15 illustrate how the shoulder strap 135 is connected to the adjuster 153. To adjust the length of the shoulder strap 135, the adjuster 153 and the second end 135b may be moved along the length of the intermediate portion 135c by sliding the intermediate portion 135c through the slots 166, 167, and 148a. The adjuster 153 preferably does not come into contact with the patient's skin to aid in the comfort of the holster 115.

The junction 140 is preferably an upside down T-shaped member interconnecting the shoulder strap 135 and the chest strap 152 and including a top portion 141 and a bottom portion 147. An opening 150 is formed between the shoulder strap 135 and the chest strap 152 through which the patient's arm is inserted to don the holster 115. The connector 148 interconnects the shoulder strap 135 and the top portion 141. The bottom portion 147 includes a left portion 142, a right portion 143, and a channel 146 extending through the bottom portion 147. The channel 146 is preferably wide enough to accommodate the chest strap 152 and slide the chest strap 152, including an adjuster 153, therethrough. Within the channel 146 are two fasteners 149 proximate the left and right portions 142 and 143.

The chest strap 152 includes a first end 152a, a second end 152b, and an intermediate portion 152c between the first end 152a and the second end 152b. The first end 152a is connected to a buckle portion 154 and the second end 152b is connected to an adjuster 153 in a similar manner as the second end 135b of the shoulder strap 135 is connected to an adjuster 153. The intermediate portion 152c is routed through slots 166 and 167 of the adjuster 153 and through a slot (not shown) of a buckle portion 157. To adjust the length of the chest strap 152, the adjuster 153 and the second end 152b may be moved along the length of the intermediate portion 152c by sliding the intermediate portion 152c through the slots 166 and 167 and through the slot in the buckle portion 157. The intermediate portion 152c includes a position indicator 145 proximate a left portion of the chest strap 152, as shown in FIG. 3, and a position indicator 156 proximate a right portion of the chest strap 152, as shown in FIG. 4. A mating fastener 144 is located on each side of the position indicator 145, and a mating fastener 155 is located on each side of the position indicator 156. The mating fasteners 144 and 155 are each configured and arranged to mate with the fasteners 149 within the channel 146 of the junction 140 to secure the chest strap 152 to the junction 140.

Figure 17:
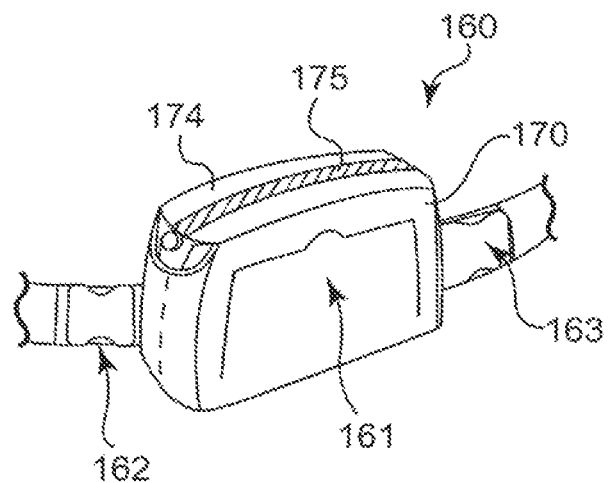
FIG. 17 is a front perspective view of a rechargeable power source holder of the holster shown in FIG. 3.
Figure 18:
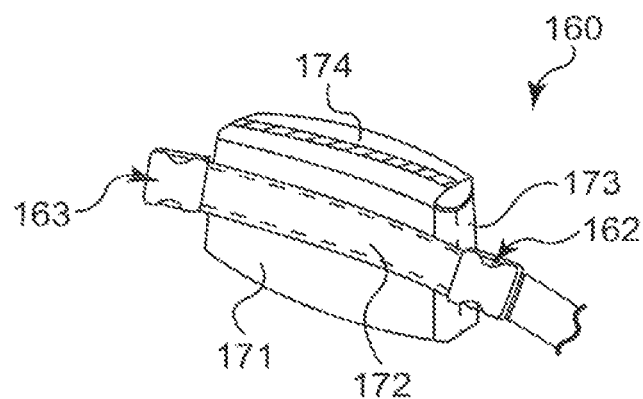
FIG. 18 is a rear perspective view of the rechargeable power source holder shown in FIG. 17.

As shown in FIGS. 17 and 18, the charging unit holder 160 includes sides 173 and a top 174 interconnecting a front 170 and a back 171 to form a cavity 164 therebetween. A zipper 175 in the top 174 provides access to the cavity 164 in which the charging unit 109 is housed. The front 170 includes an access panel 161, which may be opened, as shown in FIG. 8, to reveal the charging unit 109. A strap 172 is connected to the back 171 and a buckle portion 162 is connected to one end and a buckle portion 163 is connected to the other end proximate opposing sides of the charging unit holder 160.

Figure 5:
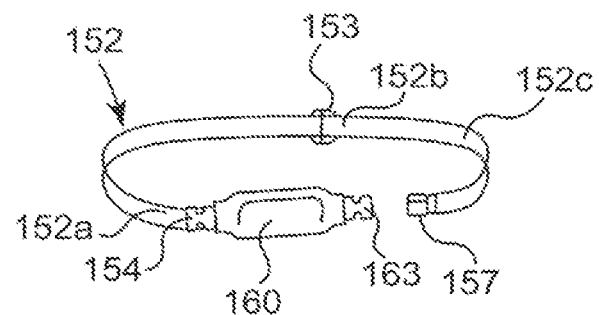
FIG. 5 is a front perspective view of a portion of the holster shown in FIG. 3 for charging a pectorally implanted medical device.
Figure 11:
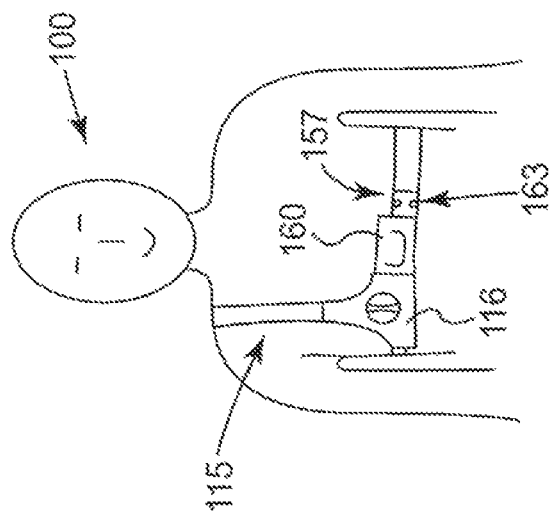
FIG. 11 illustrates a patient donning the holster shown in FIG. 3 on the patient's left side.
Figure 12:
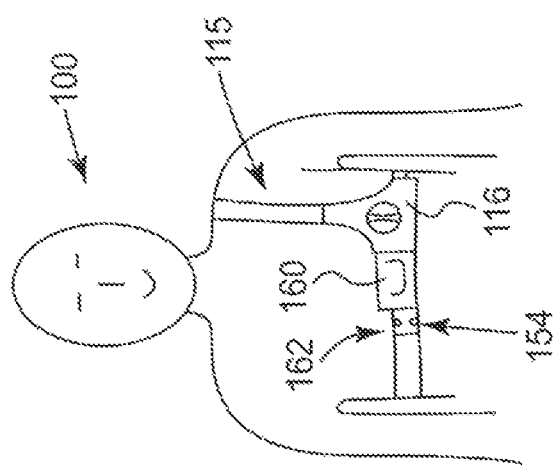
FIG. 12 illustrates a patient donning the holster shown in FIG. 3 on the patient's right side.

The holster 115 is versatile as it may be donned in a first configuration on the patient's right side as illustrated in FIGS. 3 and 12, in a second configuration on the patient's left side as illustrated in FIGS. 4 and 11, or in a third configuration as a waist belt as illustrated in FIG. 5. The buckle portions 133, 157, and 162 are preferably male buckle portions, and the buckle portions 132, 154, and 163 are preferably female mating buckle portions. The male buckle portions are releasably connectable to the female buckle portions. This enables the charging unit holder 160 to be positioned on either side of the antenna holder 116 or to be used with the chest strap 152 as a waist belt. Alternatively, the charging unit holder 160 could be eliminated from the holster 115.

For a pectorally implanted medical device in the patient's right pectoral region, the buckle portion 162 of the charging unit holder 160 is connected to the buckle portion 132 of the antenna holder 116, and the buckle portion 133 of the antenna holder 116 is connected to the buckle portion 154 of the chest strap 152. These connections are preferably hidden from view between the first and second panels 117 and 119 of the antenna holder 116. The buckle portion 163 of the charging unit holder 160 is connected to the buckle portion 157 of the chest strap 152 and serves as the main buckle the patient uses to secure and release the holster 115. Once the holster 115 has been adjusted to fit the patient, only the main buckle needs to be secured and released to don the holster 115 and the other buckle portions can remain secured. The fasteners 155 of the chest strap 152 are connected to the fasteners 149 of the junction 140 and the position indicator 145 provides indication that the longer portion of the chest strap 152 should be positioned proximate the patient's left side thereby positioning the antenna holder 116 proximate the patient's right side.

For a pectorally implanted medical device in the patient's left pectoral region, the buckle portion 163 of the charging unit holder 160 is connected to the buckle portion 133 of the antenna holder 116, and the buckle portion 132 of the antenna holder 116 is connected to the buckle portion 157 of the chest strap 152. These connections are preferably hidden from view between the first and second panels 117 and 119 of the antenna holder 116. The buckle portion 162 of the charging unit holder 160 is connected to the buckle portion 154 of the chest strap 152 and serves as the main buckle the patient uses to secure and release the holster 115. Once the holster 115 has been adjusted to fit the patient, only the main buckle needs to be secured and released to don the holster 115 and the other buckle portions can remain secured. The fasteners 144 of the chest strap 152 are connected to the fasteners 149 of the junction 140 and the position indicator 156 provides indication that the longer portion of the chest strap 152 should be positioned proximate the patient's right side thereby positioning the antenna holder 116 proximate the patient's left side.

Alternatively, the charging unit holder 160 could be eliminated from the holster 115 and the buckle portion 154 could be connected to the buckle portion 127 and the buckle portion 132 could be connected to the buckle portion 157.

For use as a waist belt, the antenna holder 116, the shoulder strap 135, and the junction 140 are removed from the holster 115 leaving the chest strap 152 and the charging unit holder 160. Preferably, the buckle portion 163 of the charging unit holder 160 is connected to the buckle portion 157 of the chest strap 152 and the buckle portion 162 of the charging unit holder 160 is connected to the buckle portion 154 of the chest strap 152. The antenna 107 is then either manually held proximate the pectorally implanted medical device 103 or held by other suitable means known in the art.

Regardless how the holster 115 is donned by the patient, the antenna 107 is placed within the cavity 134 and the openings 118 and 120 of the antenna holder 116 and the charging unit 109 is placed within the cavity 164 of the charging unit holder 160. The cable 108 interconnects the antenna 107 and the charging unit 109, and any excess cable 108 may be stored within the cavity 134 of the antenna holder 116. In FIG. 8, the charging unit 109 is shown operatively connected to a cable 110 which operatively connects the charging unit 109 to a power source such as a wall outlet. The cable 110 is preferably only used when the charging unit 109 is being charged and may be removed to allow the patient to be ambulatory during charging of the pectorally implanted medical device.

To don the holster 115, it is first determined on which side of the patient the pectorally implanted medical device is located, and then the holster 115 is configured accordingly. Then, the patient inserts the patient's arm through the shoulder strap 135 and through the opening 150 between the shoulder strap 135 and the chest strap 152. After the pectorally implanted medical device 103 has been located, the antenna 107 is then placed proximate the pectorally implanted medical device 103. For a pectorally implanted medical device on the patient's right side, the main buckle is the connection between the buckle portion 163 of the charging unit holder 160 and the buckle portion 157 of the chest strap 152 and serves as the main buckle the patient uses to secure and release the holster 115. For a pectorally implanted medical device on the patient's left side, the main buckle is the connection between the buckle portion 162 of the charging unit holder 160 and the buckle portion 154 of the chest strap 152 and serves as the main buckle the patient uses to secure and release the holster 115. The shoulder strap 135 and the chest strap 152 may be adjusted using the adjusters 153 as needed to ensure that the antenna 107 is proximate the pectorally implanted medical device 103. For a shorter charge time of the pectorally implanted medical device 103, the center of the antenna 107 should be placed over the center of the pectorally implanted medical device 103. The antenna 107 should not be moved around or the charge time could be increased. Also, the less tissue there is between the pectorally implanted medical device 103 and the antenna 107, the shorter the charge time will be.

Figure 9:
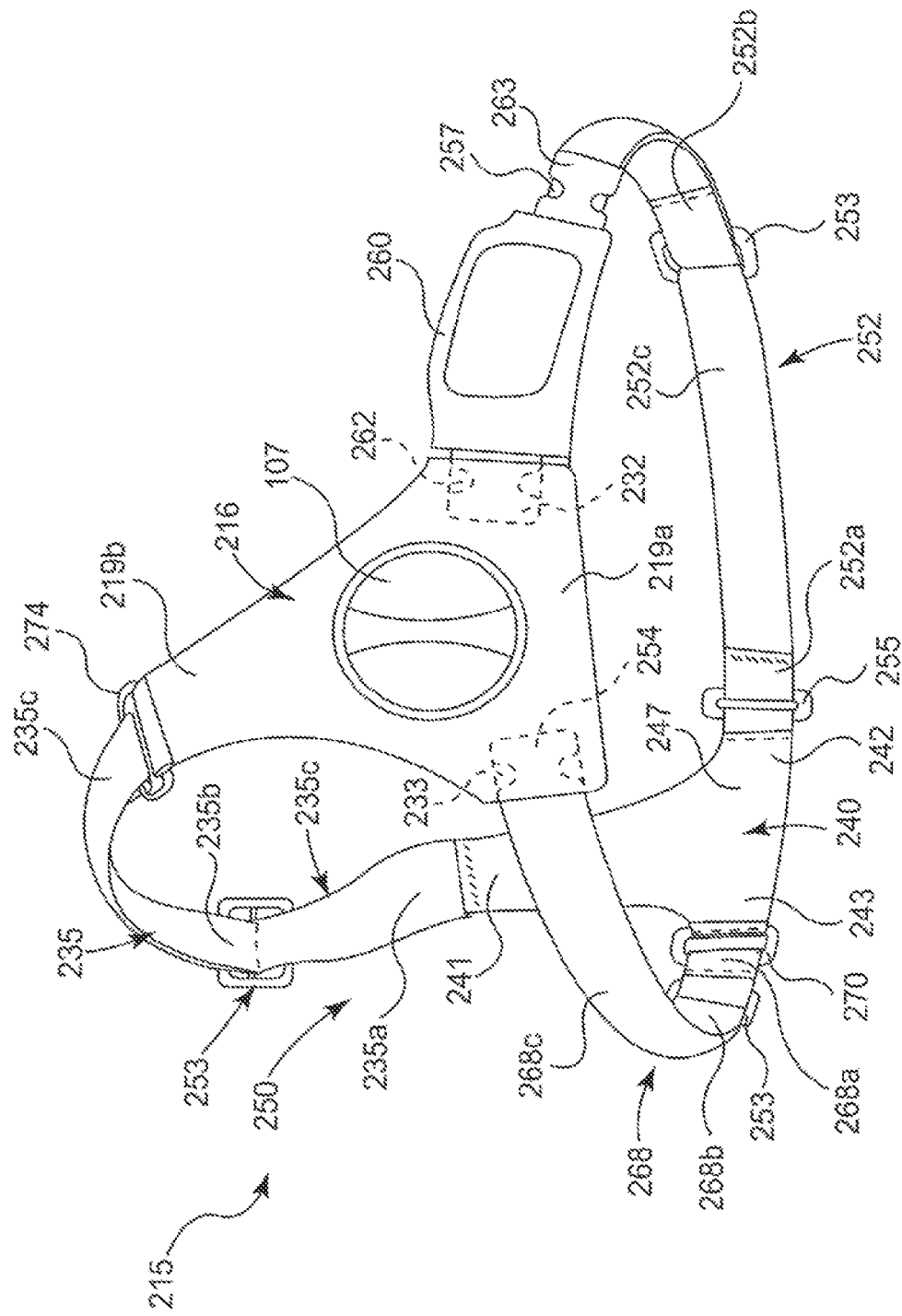
FIG. 9 is a front perspective view of another embodiment holster constructed according to the principles of the present disclosure.

Another embodiment holster 215 is shown in FIG. 9. The holster 215 includes an antenna holder 216, a shoulder strap 235, a left chest strap 252, a right chest strap 268, and a charging unit holder 260. The antenna holder 216 includes a first panel 217 and a second panel 219 forming a cavity 234 therebetween configured and arranged to house an antenna 107. The first panel 217 and the second panel 219 are similarly constructed. The first panel 217 preferably includes a rectangular base portion 217a with a truncated triangular portion 217b having concave sides extending upward from the rectangular base portion 217a. The first panel 217 has a top portion 225 proximate the top of the truncated triangular portion 217b and a left portion 226 and a right portion 227 proximate opposing sides of the rectangular base portion 217a. The second panel 219 also includes a rectangular base portion 219a with a truncated triangular portion 219b having concave sides extending upward from the rectangular base portion 219b. The second panel 219 has a top portion 228 proximate the top of the truncated triangular portion 219b and a left portion 229 and a right portion 230 proximate opposing sides of the rectangular base portion 219a. The first panel 217 is the inner layer proximate the patient's skin and the second panel 219 is the outer layer. The first panel 217 and the second panel 219 are approximately the same size and include corresponding circular openings (not shown) with the opening in the second panel 219 preferably being slightly larger in diameter than the opening in the first panel 217. The opening in the first panel 217 allows the antenna 107 to contact the patient's skin, and the opening in the second panel 219 provides access to the antenna 107. Stitching (not shown) is preferably used to connect the first panel 217 and the second panel 219 together and to hold the antenna 107 in place within the cavity 234. In addition, a fastener (not shown) such as hook and loop may be connected to the outer surface of the top portion 225 and to the inner surface of the top portion 228 so that the top portions 225 and 228 are releasably connectable to allow access to the cavity 234.

The shoulder strap 235 includes a first end 235a, a second end 235b, and an intermediate portion 235c between the first end 235a and the second end 235b. The first end 235a is connected to a top portion 241 of a junction 240 and the second end 235b is connected to an adjuster 253. The intermediate portion 235c of the shoulder strap 235 is routed through slots in the adjuster 253 and through a slot of a connector 274, which connects the intermediate portion 235c to the top portions 225 and 228 of the antenna holder 216. To adjust the length of the shoulder strap 235, the adjuster 253 and the second end 235b may be moved along the length of the intermediate portion 235c by sliding the intermediate portion 235c through the slots in the adjuster 253 and the connector 274. The adjuster 253 preferably does not come into contact with the patient's skin to aid in the comfort of the holster 215.

The junction 240 is preferably an upside down T-shaped member interconnecting the shoulder strap 235 and the left and right chest straps 252 and 268 and including a top portion 241 and a bottom portion 247. As shown in FIG. 9, an opening 250 is formed between the shoulder strap 235 and the chest strap 252 through which the patient's arm is inserted to don the holster 215 for a pectorally implanted medical device on the patient's right side. The bottom portion 247 includes a left portion 242 connected to a connector 255 and a right portion 243 connected to a connector 270.

The left chest strap 252 includes a first end 252a, a second end 252b, and an intermediate portion 252c between the first end 252a and the second end 252b. The first end 252a is connected to the connector 255 and the second end 252b is connected to an adjuster 253 in a similar manner as the second end 235b of the shoulder strap 235 is connected to an adjuster 253. The intermediate portion 252c is routed through slots (not shown) in the adjuster 253 and through a slot (not shown) of a buckle portion 257. To adjust the length of the left chest strap 252, the adjuster 253 and the second end 252b may be moved along the length of the intermediate portion 252c by sliding the intermediate portion 252c through the slots in the adjuster 253 and the buckle portion 257.

The right chest strap 268 includes a first end 268a, a second end 268b, and an intermediate portion 268c between the first end 268a and the second end 268b. The first end 268a is connected to the connector 270 and the second end is connected to an adjuster 253 in a similar manner as the second end 235b of the shoulder strap 235 is connected to an adjuster 253. The intermediate portion 268c is routed through slots (not shown) in the adjuster 253 and through a slot (not shown) of a buckle portion 254. To adjust the length of the right chest strap 268, the adjuster 253 and the second end 268b may be moved along the length of the intermediate portion 268c by sliding the intermediate portion 268c through the slots in the adjuster 253 and the buckle portion 254.

The charging unit holder 260 is preferably rectangular in shape and includes an access panel 261 which may be opened to reveal the charging unit housed therein. A buckle portion 263 is connected to the left end and a buckle portion 262 is connected to the right end of the charging unit holder 260.

Figure 10:
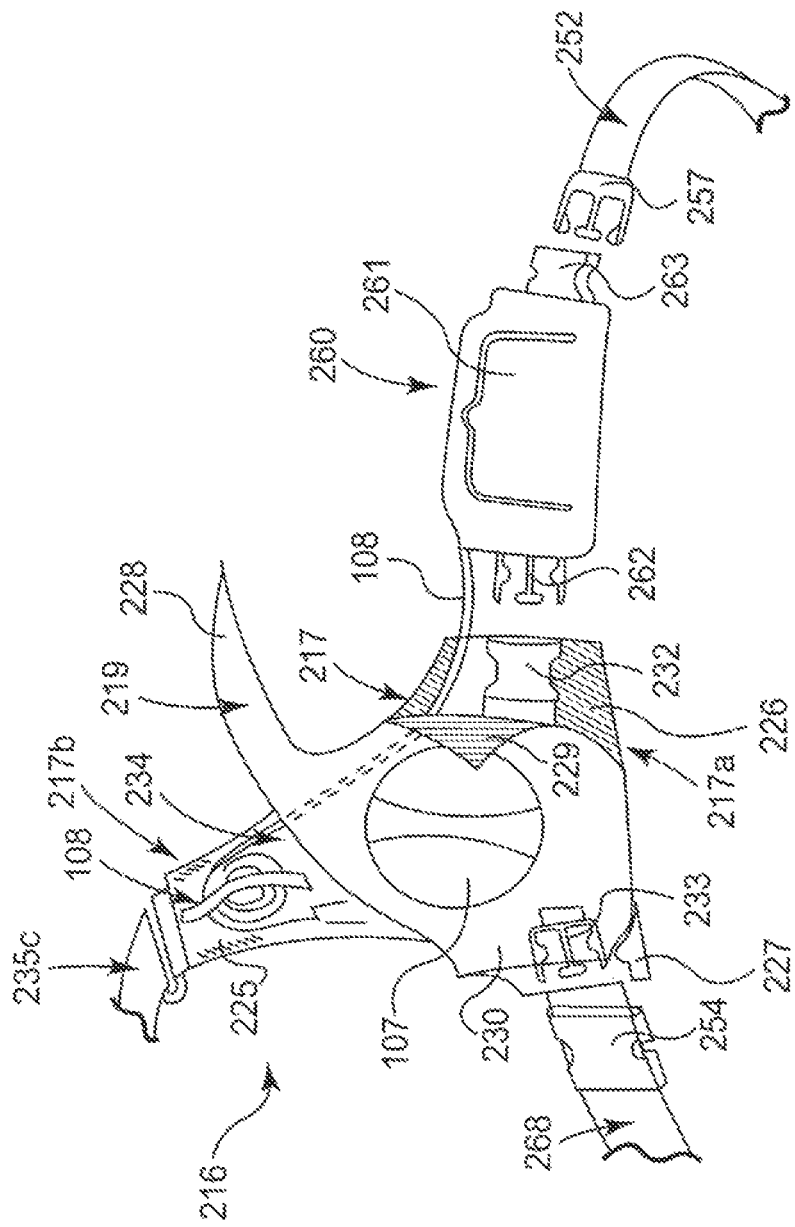
FIG. 10 is a front perspective view of an antenna holder of the holster shown in FIG. 9 with a front panel in an open position.

FIG. 10 shows the top portion 228 peeled away from the top portion 225 to expose the cable 108, the left portion 229 peeled away from the left portion 226 to expose the buckle portion 232, and the right portion 230 peeled away from the right portion 227 to expose the buckle portion 254.

The holster 215 is versatile as it may be donned in a first configuration on the patient's right side as illustrated in FIG. 9 or in a second configuration on the patient's left side (not shown). The buckle portions 233, 257, and 262 are preferably male buckle portions, and the buckle portions 232, 254, and 263 are preferably female mating buckle portions. The male buckle portions are releasably connectable to the female buckle portions. This enables the charging unit holder 260 to be positioned on either side of the antenna holder 216 for donning on either the right or the left side of the patient. Alternatively, the charging unit holder 260 could be eliminated from the holster 215.

For a pectorally implanted medical device in the patient's right pectoral region, the buckle portion 262 of the charging unit holder 260 is connected to the buckle portion 232 of the antenna holder 216, and the buckle portion 233 of the antenna holder 216 is connected to the buckle portion 254 of the right chest strap 268. These connections are preferably hidden from view between the first and second panels 217 and 219 of the antenna holder 216. The buckle portion 263 of the charging unit holder 260 is connected to the buckle portion 257 of the left chest strap 252 and serves as the main buckle the patient uses to secure and release the holster 215. Once the holster 215 has been adjusted to fit the patient, only the main buckle needs to be secured and released to don the holster 215 and the other buckle portions can remain secured.

For a pectorally implanted medical device in the patient's left pectoral region, which is not shown, the buckle portion 263 of the charging unit holder 260 is connected to the buckle portion 233 of the antenna holder 216, and the buckle portion 232 of the antenna holder 216 is connected to the buckle portion 257 of the left chest strap 252. These connections are preferably hidden from view between the first and second panels 217 and 219 of the antenna holder 216. The buckle portion 262 of the charging unit holder 260 is connected to the buckle portion 254 of the right chest strap 268 and serves as the main buckle the patient uses to secure and release the holster 215. Once the holster 215 has been adjusted to fit the patient, only the main buckle needs to be secured and released to don the holster 215 and the other buckle portions can remain secured.

Alternatively, the charging unit holder 260 could be eliminated from the holster 215 and the buckle portion 254 could be connected to the buckle portion 227 and the buckle portion 232 could be connected to the buckle portion 257. Alternatively, the antenna holder 216 and the shoulder strap 235 could be eliminated from the holster 215 and used as a waist belt.

To don the holster 215, it is first determined on which side of the patient the pectorally implanted medical device is located, and then the holster 215 is configured accordingly. Then, the patient inserts the patient's arm through the shoulder strap 235 and through the opening 250 between the shoulder strap 235 and either the left chest strap 252 or the right chest strap 268. After the pectorally implanted medical device has been located, the antenna 107 is then placed proximate the pectorally implanted medical device. For a pectorally implanted medical device on the patient's right side, the main buckle is the connection between the buckle portion 263 of the charging unit holder 260 and the buckle portion 257 of the left chest strap 252 and serves as the main buckle the patient uses to secure and release the holster 215. For a pectorally implanted medical device on the patient's left side, the main buckle is the connection between the buckle portion 262 of the charging unit holder 260 and the buckle portion 254 of the right chest strap 268 and serves as the main buckle the patient uses to secure and release the holster 215. The shoulder strap 235 and the chest straps 252 and 268 may be adjusted using the adjusters 253 as needed to ensure that the antenna 107 is proximate the pectorally implanted medical device.

Figure 19:
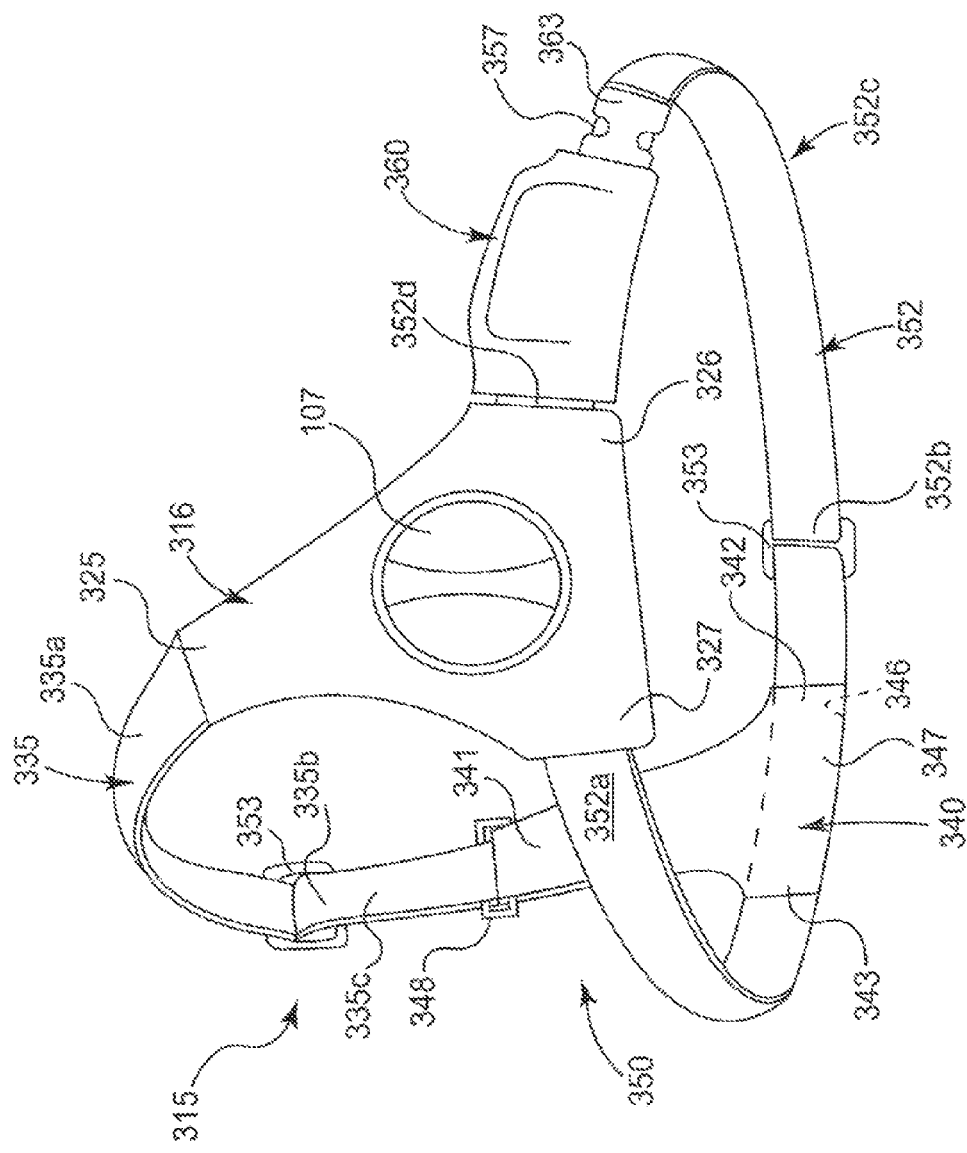
FIG. 19 is a front perspective view of another embodiment holster constructed according to the principles of the present disclosure.
Figure 20:
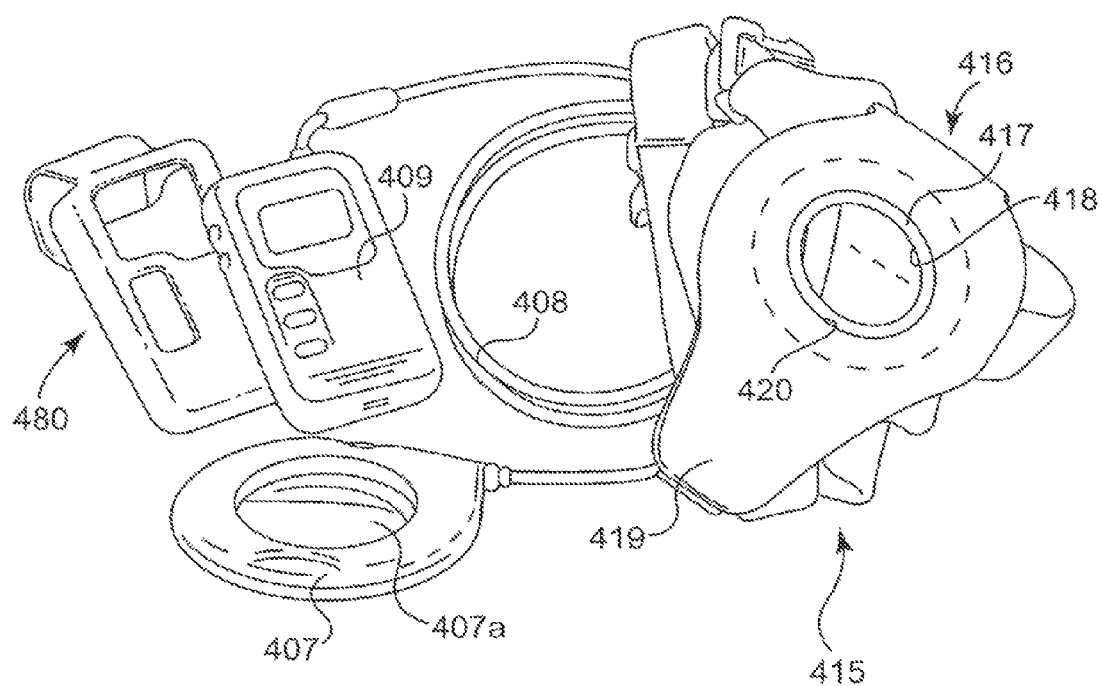
FIG. 20 is a perspective view of a recharging system including a charging unit holder, a charging unit, an antenna, and another embodiment holster constructed according to the principles of the present disclosure.

Another embodiment holster 315 is shown in FIG. 19. The holster 315 includes an antenna holder 316, a shoulder strap 335, a chest strap 352, and a charging unit holder 360. The antenna holder 316 is preferably constructed similarly to the antenna holders 116 and 216 and is configured and arranged to house an antenna 107.

The shoulder strap 335 includes a first end 335a, a second end 335b, and an intermediate portion 335c between the first end 335a and the second end 335b. The first end 335a is connected to a top portion 325 of the antenna holder 316, and the second end 335b is connected to an adjuster 353. The intermediate portion 335c of the shoulder strap 335 is routed through slots in the adjuster 353 and through a slot of a connector 348, which connects the intermediate portion 335c to a junction 340. To adjust the length of the shoulder strap 335, the adjuster 353 and the second end 335b may be moved along the length of the intermediate portion 335c by sliding the intermediate portion 335c through the slots of the adjuster 353 and the connector 348. The adjuster 353 preferably does not come into contact with the patient's skin to aid in the comfort of the holster 315.

The junction 340 is preferably an upside down T-shaped member interconnecting the shoulder strap 335 and the chest strap 352 and including a top portion 341 and a bottom portion 347. An opening 350 is formed between the shoulder strap 335 and the chest strap 352 through which the patient's arm is inserted to don the holster 315. The connector 348 interconnects the shoulder strap 335 and the top portion 341. The bottom portion 347 includes a left portion 342, a right portion 343, and a channel 346 extending through the bottom portion 347. The channel 346 is preferably wide enough to accommodate the chest strap 352 and slide the chest strap 352, including an adjuster 353, therethrough.

The chest strap 352 includes a first end 352a, a second end 352b, an intermediate portion 352c between the first end 352a and the second end 352b, and an optional extension portion 352d. The first end 352a is connected to the right side 327 of the antenna holder 316 and the second end 352b is connected to an adjuster 353 in a similar manner as the second end 335b of the shoulder strap 335 is connected to an adjuster 353. One end of the extension portion 352d is connected to the left side 326 of the antenna holder 316 and the other end is connected to a buckle portion 363. The extension portion 352d is optional as the buckle portion 363 could be connected to the left side 326 of the antenna holder 316. The intermediate portion 352c is routed through slots (not shown) of the adjuster 353 and through a slot (not shown) of a buckle portion 357. The buckle portions 363 and 357 are mating buckle portions. To adjust the length of the chest strap 352, the adjuster 353 and the second end 352b may be moved along the length of the intermediate portion 352c by sliding the intermediate portion 352c through the slots of the adjuster 353 and the buckle portion 357.

The charging unit holder 360 is preferably constructed similarly to the charging unit holders 160 and 260 and is configured and arranged to house a charging unit but does not include a strap with buckles connected to the back. Rather, a fastener (not shown) is preferably connected to the back and is configured and arranged to be releasably connected to a mating fastener (not shown) connected to the chest strap 352 or to the shoulder strap 335. These mating fasteners are preferably hook and loop, snaps, or other suitable mating fasteners that would allow the charging unit holder 360 to be releasably connected to the chest strap 352 or to the shoulder strap 335. The charging unit holder 360 may be positioned and repositioned at any suitable location along the length of the chest strap 352 or the shoulder strap. Alternatively, the charging unit holder 360 may be placed in the patient's pocket, around the patient's waist using a waist belt, or any other suitable location.

The holster 315 is versatile as it may be donned in a first configuration on the patient's right side as illustrated in FIG. 19 or it may be donned in a second configuration on the patient's left side. The shoulder strap 335 may be placed on either the right or the left shoulder of the patient, and the charging unit holder 360 may be positioned anywhere along the length of the chest strap 352 or the shoulder strap 335.

To don the holster 315, it is first determined on which side of the patient the pectorally implanted medical device is located, and then the holster 315 is configured accordingly. Then, the patient inserts the patient's arm through the shoulder strap 335 and through the opening 350 between the shoulder strap 335 and the chest strap 352. The buckle portions 363 and 357 are then connected. After the pectorally implanted medical device 103 has been located, the antenna 107 is then placed proximate the pectorally implanted medical device 103. The shoulder strap 335 and the chest strap 352 may be adjusted using the adjusters 353 as needed to ensure that the antenna 107 is proximate the pectorally implanted medical device 103. For a shorter charge time of the pectorally implanted medical device 103, the center of the antenna 107 should be placed over the center of the pectorally implanted medical device 103. The antenna 107 should not be moved around or the charge time could be increased. Also, the less tissue there is between the pectorally implanted medical device 103 and the antenna 107, the shorter the charge time will be.

Another embodiment holster 415 is shown in FIGS. 20-29. The holster 415 includes an antenna holder 416, a shoulder strap 435, and a torso strap 452. An optional charging unit holder 480 may be used with the holster 415.

The antenna holder 416 is preferably constructed similarly to the antenna holders 116, 216, and 316 and is configured and arranged to house an antenna 407 including a raised portion 407a and a contact portion (not shown). The antenna holder 416 includes a first panel 417 and a second panel 419 preferably interconnected by stitching (not shown) around the edges of the panels 417 and 419. The panels 417 and 419 proximate the top of the antenna holder 416 are preferably not sewn together to allow access to a cavity 422 between the panels 417 and 419 and are releasably connected with a fastener (not shown) such as but not limited to hook and loop or a snap. The first panel 417 includes a rounded center portion 423, a top portion 425, and a bottom portion (not shown) corresponding with a rounded center portion 424, a top portion 428, and a bottom portion 429 of the second panel 419. The center portion 423 includes an opening 418 and the center portion 424 includes an opening 420. The antenna 407 is housed within the cavity 422 between the first and second panels 417 and 419 proximate the center portions 423 and 424. The center portions 423 and 424 correspond with the shape of the antenna 407 and are configured and arranged to receive the antenna 407. The shape of the center portions 423 and 424 assist in keeping the antenna 407 positioned properly within the antenna holder 416. The opening 418 is configured and arranged to expose the contact portion (not shown) and the opening 420 is configured and arranged to accommodate the raised portion 407a, which extends through the opening 420 to also assist in keeping the antenna 407 positioned properly within the antenna holder 416. Preferably, the opening 420 is larger than the opening 418. Stitching 421 is configured and arranged to hold a retaining member (not shown) in place proximate the opening 420. The retaining member is preferably a plastic ring member configured and arranged to accommodate the raised portion 407a to assist in keeping the raised portion 407a in place within the opening 420.

Proximate the bottom portions, a strap 434 is operatively connected to the antenna holder 416, preferably with stitching (not shown). The strap 434 is threaded through slots in a male buckle portion 433, which is slidably connected to the strap 434. Proximate the top portions 425 and 428, a connector 432 interconnects the antenna holder 416 to the shoulder strap 435. The shoulder strap 435 includes a first end 435a, a second end 435b, and an intermediate portion 435c between the first end 435a and the second end 435b. The first end 435a is operatively connected to an intermediate portion 452c of the torso strap 452, preferably with stitching 457. The second end 435b is operatively connected to an adjuster 436. The intermediate portion 435c of the shoulder strap 435 is routed through slots in the adjuster 436 and through a slot of the connector 432, which connects the intermediate portion 435c to the top portions 425 and 428 of the antenna holder 416. The adjuster 436 may be slid along the intermediate portion 435c to adjust the length of the shoulder strap 435. The adjuster 436 preferably does not come into contact with the patient's skin to aid in the comfort of the holster 415. Although the strap 434 is preferably a separate strap from the shoulder strap 435, the strap 434 may be considered an extension of the shoulder strap 435 functioning as a connecting strap interconnecting the shoulder strap 435 and the torso strap 452.

The torso strap 452 includes a first end 452a, a second end 452b, an intermediate portion 452c between the first end 452a and the second end 452b, and an optional elastic portion 452d of the intermediate portion 452c. The first end 452a is routed through slots in a male buckle portion 454 and the second end 452b is connected to a female buckle portion 455, which mates with the male buckle portion 454.

A first connector 460 includes a strap 461, a female buckle portion 462, and an optional hook member 463. The strap 461 is routed through a slot in the female buckle portion 462, folded back onto itself, and then connected to the hook member 463. Thus, the strap 461 includes two layers between the female buckle portion 462 and the hook member 463 through which the torso strap 452 is routed so that the first connector 460 is positioned on the intermediate portion 452c between the shoulder strap 435 and the first end 452a and may be slid along the intermediate portion 452c. A second connector 465 includes a strap 466, a female buckle portion 467, and an optional hook member 468. The strap 466 is routed through a slot in the female buckle portion 467, folded back onto itself, and then connected to the hook member 468. Thus, the strap 466 includes two layers between the female buckle portion 467 and the hook member 468 through which the torso strap 452 is routed so that the second connector 465 is positioned on the intermediate portion 452c between the shoulder strap 435 and the second end 452b and may be slid along the intermediate portion 452c. The female buckle portions 462 and 467 are configured and arranged to mate with the male buckle portion 433.

Preferably, the straps of the holster 415 are made of a nylon or a polyester material. Portions of the straps of the holster 415 may be made of an elastic material to enhance the comfort of donning the holster 415. For example, the strap 434 may be elastic, the portion 452d of the intermediate portion 452c may be elastic, and the straps 461 and 466 may be elastic.

The optional charging unit holder 480 is configured and arranged to house the charging unit 409. The charging unit holder 480 is shown in FIGS. 30 and 31. The optional charging unit holder 480 may be used as a protective sleeve for the charging unit 409 and may be used as a means for connecting the charging unit 409 to a connecting structure such as but not limited to the holster 415, a belt, a pocket, the patient's clothing, or any other suitable connecting structure. The front of the charging unit holder 480 includes a viewing window 487 proximate the top to allow the screen of the charging unit 409 to be viewed and a window 488 below the viewing window 487 to allow access to the buttons on the charging unit 409. A releasable flap 489 proximate the top of the charging unit holder 480 allows the charging unit 409 to be secured within and removed from the charging unit holder 480. A fastener (not shown), such as but not limited to hook and loop or a snap, is used to releasably connect the flap 489 to the rear of the charging unit holder 480.

The rear of the charging unit holder 480, shown in FIG. 31, may include a suitable connector for connecting the charging unit holder 480 to the connecting structure. An example of a suitable connector is a ring 481 connected proximate the bottom of the charging unit holder 480. The ring 481 may be connected to either of the hook members 463 and 468 of the holster 415, preferably with the front of the charging unit holder 480 facing away from the patient. To view the screen of the charging unit 409, the charging unit holder 480 is simply pivoted upward toward the patient so that the front of the charging unit holder 480 faces the patient. Another example of a suitable connector is a first slot 482 and a second slot 483 proximate the middle of the charging unit holder 480. The torso strap 452 or the shoulder strap 435 of the holster 415, a belt, or any other suitable elongate member may be threaded through the slots 482 and 483 to connect the charging unit holder 480 to the holster 415, the belt, or the other suitable elongate member. Another example of a suitable connector is a clip 484 that may be slid onto any suitable connecting structure. A side view of the clip 484 is shown in FIG. 32. The charging unit holder 480 may be connected, disconnected, and reconnected to any suitable connecting structure. Alternatively, the charging unit holder 480 or the charging unit 409 may be placed in the patient's pocket or even hand-held.

Figure 21:
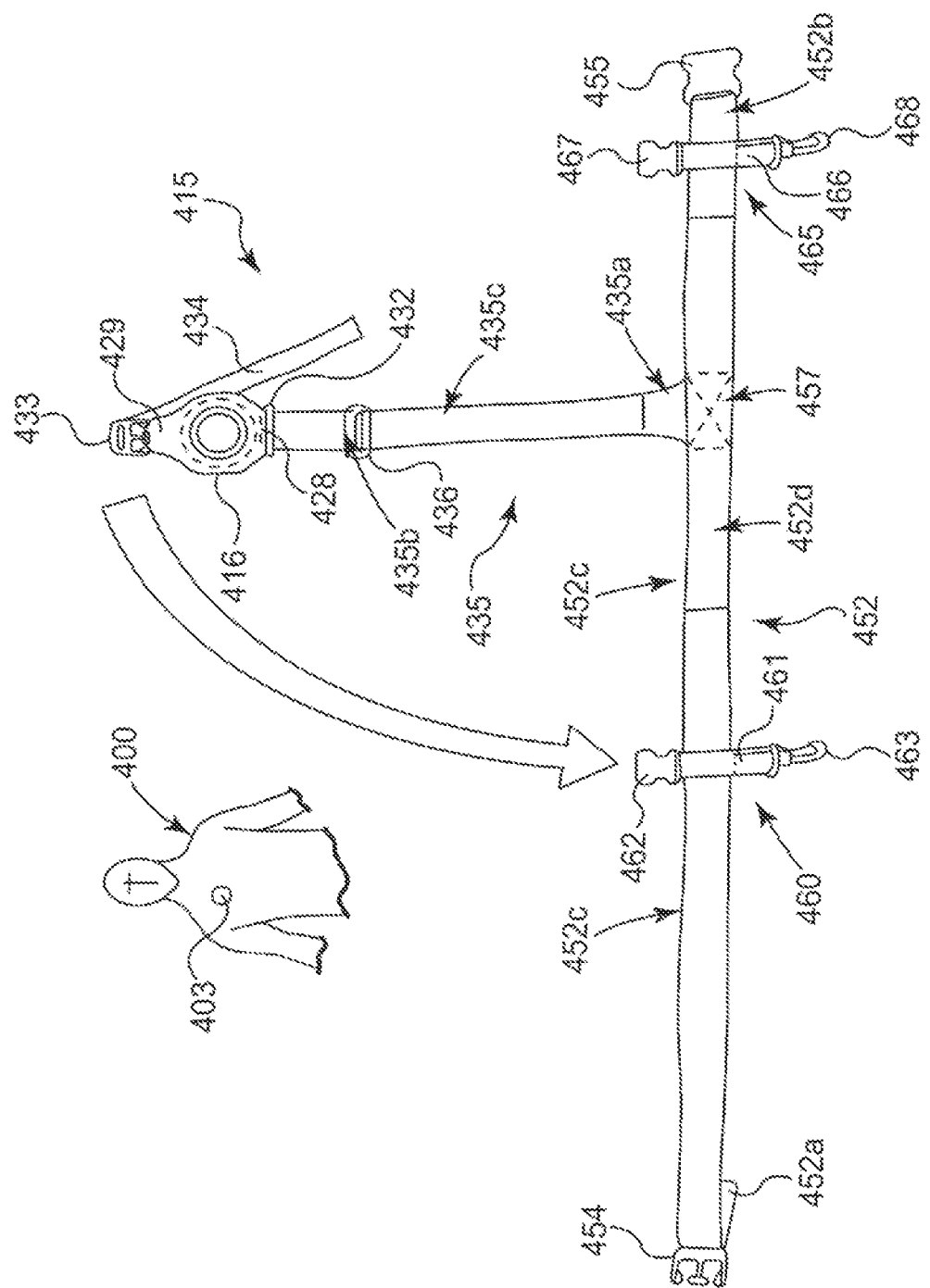
FIG. 21 is a front view of the holster shown in FIG. 20.
Figure 22:
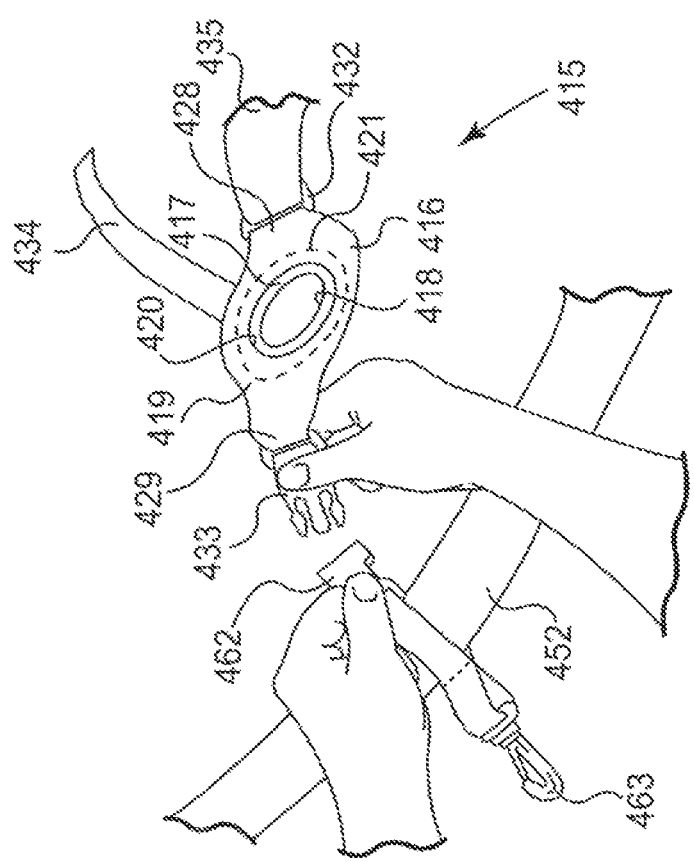
FIG. 22 is a front perspective view of a portion of the holster shown in FIG. 20 illustrating connection of an antenna holder to a torso strap of the holster.
Figure 23:
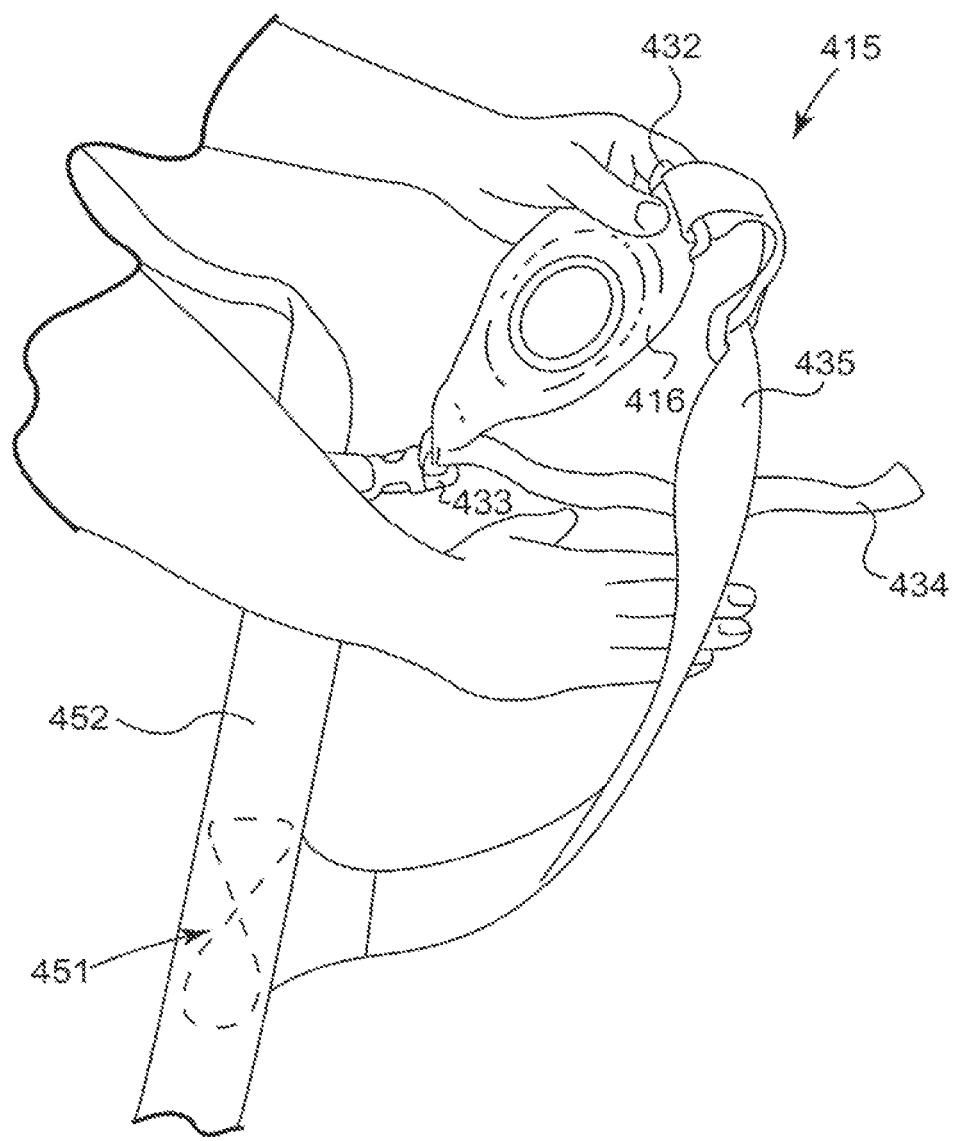
FIG. 23 is a front perspective view of a portion of the holster shown in FIG. 20 illustrating how a patient inserts the patient's right arm into an opening of a loop formed by the holster connected as shown in FIG. 22.
Figure 24:
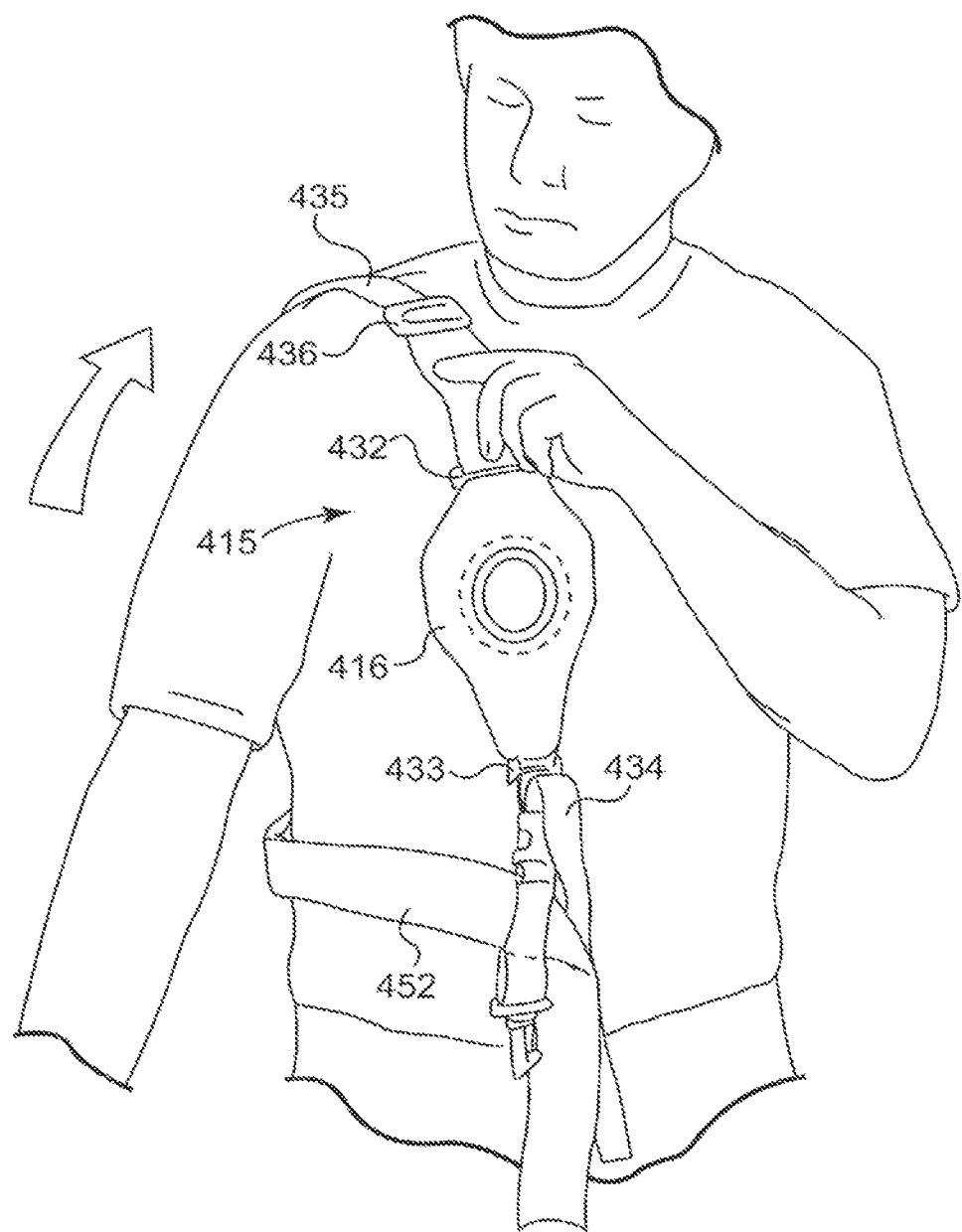
FIG. 24 is a front perspective view illustrating how the patient places the holster shown in FIG. 20 on the patient's right shoulder.
Figure 25:
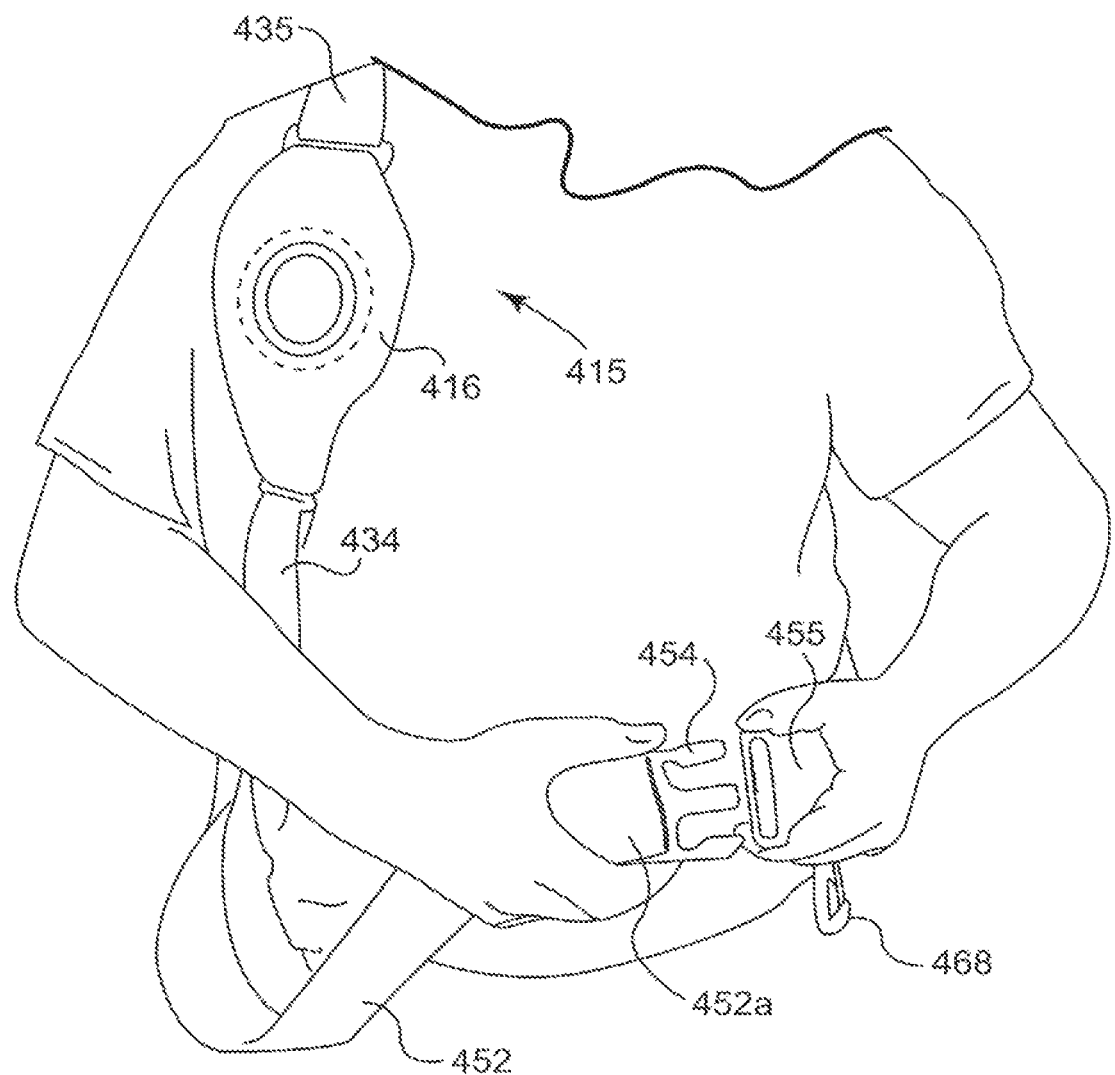
FIG. 25 is a front perspective view illustrating how the patient connects the torso strap of the holster shown in FIG. 20 about the patient's torso.
Figure 26:
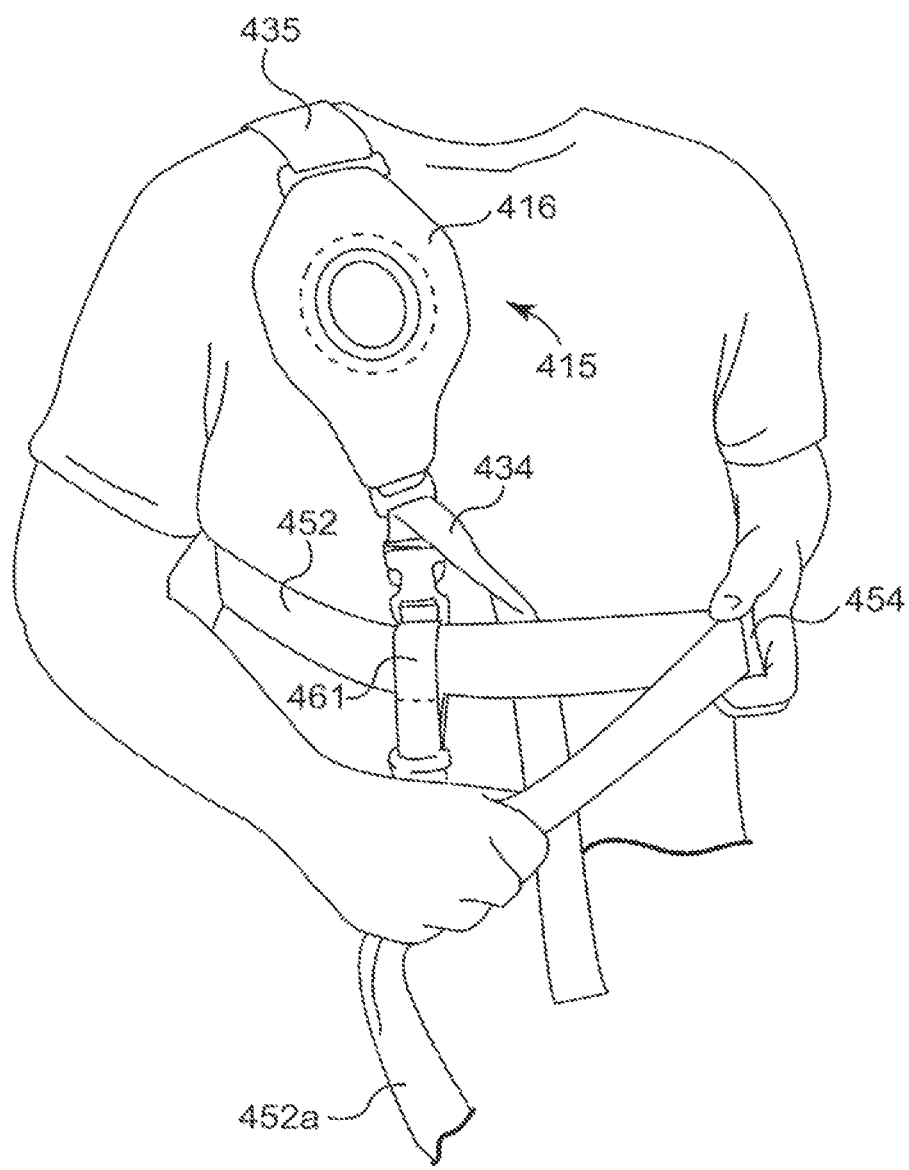
FIG. 26 is a front perspective view illustrating how the patient adjusts the torso strap of the holster shown in FIG. 20 about the patient's torso.
Figure 27:
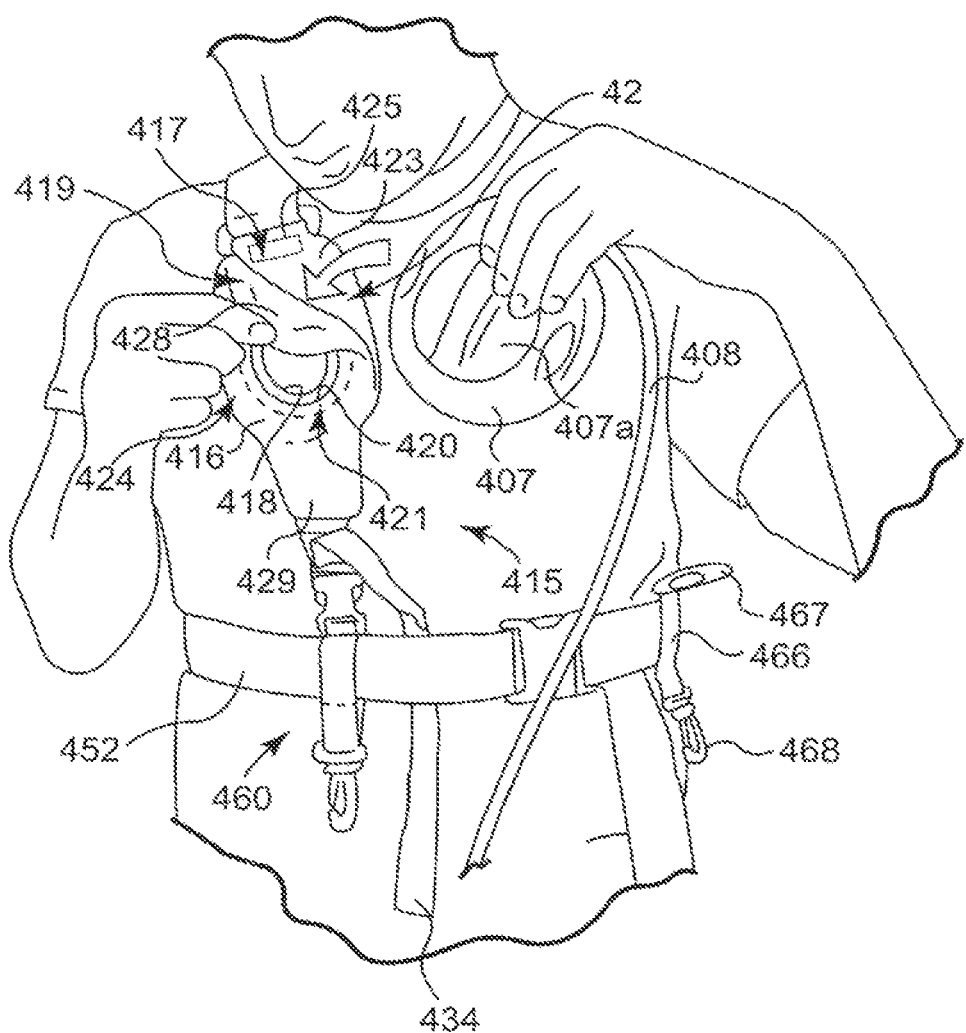
FIG. 27 is a front perspective view illustrating how the patient inserts the antenna into the antenna holder of the holster shown in FIG. 20.
Figure 28:
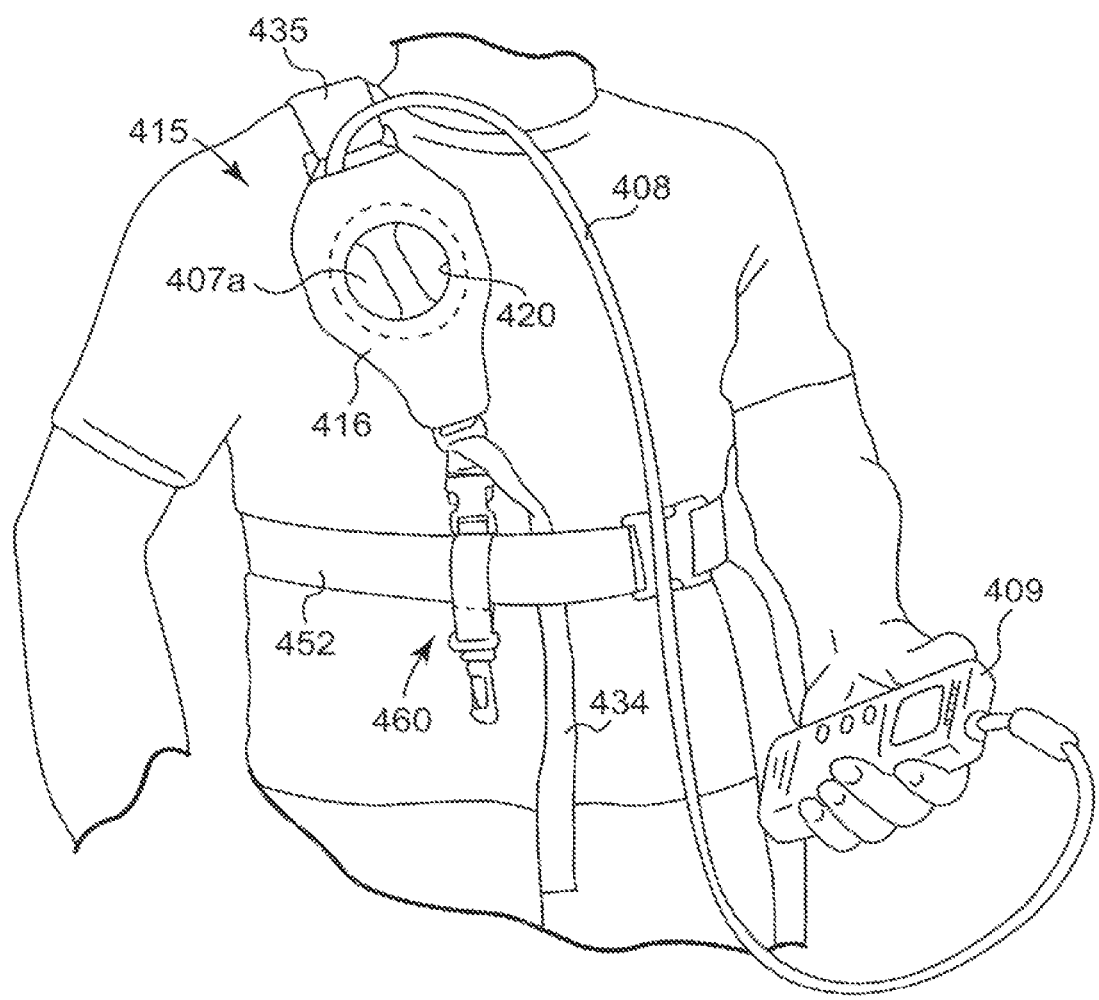
FIG. 28 is a front perspective view of the patient donning the holster shown in FIG. 20 on the patient's right side.
Figure 29:
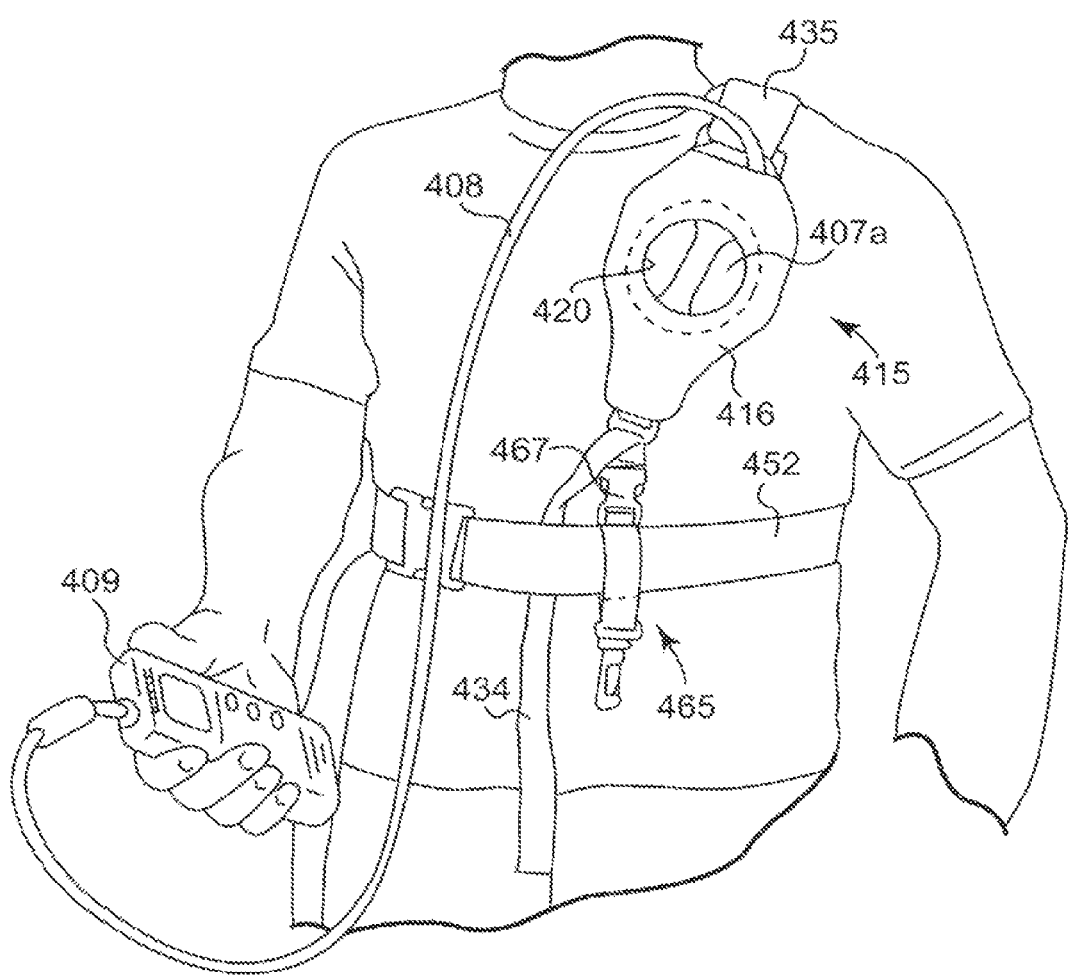
FIG. 29 is a front perspective view of the patient donning the holster shown in FIG. 20 on the patient's left side.

The holster 415 is versatile as it may be donned in a first configuration on the patient's right side as illustrated in FIG. 28 or it may be donned in a second configuration on the patient's left side as illustrated in FIG. 29. FIG. 21 shows a patient 400 with a pectoral implant 403 located proximate the patient's right pectoral region. How the holster 415 is configured to be donned on the patient's right side is illustrated in FIGS. 21-28. First, the male buckle portion 433 is connected to the female buckle portion 462 as shown in FIGS. 21 and 22 forming a loop with an opening through which the patient's right arm is inserted as shown in FIG. 23. The shoulder strap 435 is placed on the patient's right shoulder as shown in FIG. 24. Then, the torso strap 452 is positioned about the patient's torso and the male buckle portion 454 is connected to the female buckle portion 455 as shown in FIG. 25. The torso strap 452 may be tightened about the patient's torso by pulling on the torso strap 452 proximate the first end 452a thus sliding the torso strap 452 through the slots in the male buckle portion 454 as shown in FIG. 26.

After the pectorally implanted medical device 403 has been located, the antenna holder 416 is positioned proximate the pectorally implanted medical device 403. The shoulder strap 435, the torso strap 452, and the strap 461 may be adjusted as needed to ensure that the antenna holder 416 is proximate the pectorally implanted medical device 403. Preferably, to optimize the charge and to reduce the charge time, the opening 418 exposing the contact portion of the antenna 407 should correspond with the location of the pectorally implanted medical device 403. For a shorter charge time of the pectorally implanted medical device 403, the center of the antenna 407 should be placed over the center of the pectorally implanted medical device 403. The antenna 407 should not be moved around or the charge time could be increased. Also, the less tissue there is between the pectorally implanted medical device 403 and the antenna 407, the shorter the charge time will be.

To adjust the length of the torso strap 452, the first end 452a and the intermediate portion 452c proximate the first end 452a is slid through the slots in the male buckle portion 454. The torso strap 452 may be raised and lowered on the patient's torso, including the chest and the waist, so the patient can position the holster 415 where it is most comfortable. To adjust the length between the top portions 425 and 428 of the antenna holder 416 and the torso strap 452, the adjuster 436 and the second end 435b are moved along the length of the intermediate portion 435c by sliding the intermediate portion 435c through the slots of the adjuster 436 and the connector 432. To adjust the length between the bottom portions of the antenna holder 416 and the torso strap 452, the strap 434 is slid through the slots in the male buckle portion 433. The strap 461 may also be adjusted by simply sliding it to the desired location on the intermediate portion 452c.

The antenna 407 is then placed within the cavity 422 of the antenna holder 416 by separating the first and second panels 417 and 419, inserting the antenna 407 between the panels 417 and 419, and positioning the raised portion 407a of the antenna 407 so that it extends through the opening 420. This is shown in FIG. 27. The first and second panels 417 and 419 are then connected to secure the antenna 407 within the antenna holder 416.

If the pectoral implant 403 is located proximate the patient's left pectoral region, the male buckle portion 433 is connected to the female buckle portion 467. The holster 415 is then configured to be donned proximate the patient's left side similarly as described with respect the patient's right side. The holster 415 is shown donned on the patient's left side in FIG. 29.

FIGS. 28 and 29 show the patient holding the charging unit 409 connected to the antenna 407 with a cable 408. The charging unit 409 may be placed in a pocket or in the charging unit holder 480 and connected to a connecting structure.

Holsters 115, 215, 315, and 415 are reversible and adjustable so that they may be used to accommodate most all patients with pectorally implanted medical devices. The features of the holsters 115, 215, 315, and 415 may be interchanged among the embodiments. Holsters 115, 215, 315, and 415 may be made of any suitable material and are preferably made of a breathable material and may even be made of an elastic material or a moisture wicking material.

The above specification, examples and data provide a complete description of the manufacture and use of the composition of the disclosed aspects. Since many embodiments of the disclosed aspects can be made without departing from the spirit and scope of the disclosure, the invention resides in the claims hereinafter appended.

We claim:

1. A system to transcutaneously charge a power supply of an implantable device adapted to be implanted in a patient, comprising:
a charging unit;
an antenna coupled to the charging unit;
a strap comprising a shoulder strap portion adapted to be supported by the shoulder of the patient and a second strap portion adapted to encircle a portion of the patient; and
an antenna holder carried by the strap, the antenna holder comprising a cavity and being positionable to a location proximate the implantable device, the cavity adapted to receive the antenna.

2. The system of claim 1, wherein the second strap portion is adapted to receive the chest of the patient.

3. The system of claim 1, wherein the second strap portion is adapted to receive the waist of the patient.

4. The system of claim 1, wherein the shoulder strap portion is removable.

5. The system of claim 1, wherein at least one of the shoulder strap portion and the second strap portion is adjustable.

6. The system of claim 1, wherein the antenna holder comprises a top, a first side, and a second side, wherein the second strap portion further comprises a first end, a second end, and an intermediate portion, and wherein the shoulder strap portion has a third end and a fourth end, the first end being operatively connected to the first side of the antenna holder, the second end being releasably connectable to the second side of the antenna holder, the third end being operatively connected to the top of the antenna holder and the fourth end being operatively connected to the intermediate portion of the second strap portion.

7. The system of claim 1, wherein the antenna holder comprises a top, a bottom, and first and second sides, wherein the second strap portion further comprises a first end, a second end, and an intermediate portion, and wherein the shoulder strap portion comprises a third end and a fourth end, the top being operatively connected to the third end, the bottom being releasably connectable to the intermediate portion, the fourth end being operatively connected to the intermediate portion, and the first and second ends being releasably connectable.

8. The system of claim 1, further comprising a charging unit holder adapted to receive the charging unit.

9. The system of claim 8, wherein the charging unit holder may be positioned anywhere along the shoulder strap portion or anywhere along the second strap portion.

10. The system of claim 1, further comprising the implantable medical device.

11. The system of claim 1, wherein the antenna holder is adapted to keep the antenna in a predetermined position within the cavity.

12. The system of claim 1, wherein the antenna holder comprises an opening to allow access to at least a portion of the antenna when the antenna is positioned within the cavity.

13. The system of claim 1, wherein the antenna holder comprises an opening to allow a portion of the antenna to be positioned in proximity to a portion of the patient.

14. The system of claim 1, wherein the antenna holder comprises an opening adapted to accommodate a predetermined portion of the antenna.

15. The system of claim 1, wherein the charging unit comprises a rechargeable power source.

16. A system, comprising:
a charging unit;
an antenna coupled to the charging unit;
an implantable device adapted to receive energy from the charging unit;
a strap comprising a shoulder strap portion adapted to be supported by the shoulder of the patient; and
an antenna holder carried by the strap, the antenna holder comprising a cavity and being positionable to a location proximate the implantable device, the cavity adapted to receive the antenna.

17. The system of claim 16, further comprising a second strap portion adapted to receive the chest of the patient.

18. The system of claim 16, further comprising a second strap portion adapted to receive the waist of the patient.

19. The system of claim 16, wherein the shoulder strap portion is adjustable.

20. The system of claim 16, wherein the antenna holder comprises a top, wherein the shoulder strap portion further comprises an end operatively connected to the top of the antenna holder.

21. The system of claim 20, further comprising a second strap portion comprising a first end and a second end, and wherein the antenna holder further comprises a first side connected to the first end of the second strap portion and a second side connected to the second end of the second strap portion.

22. The system of claim 20, further comprising a second strap portion, and wherein the shoulder strap portion is slidably positionable relative to the second strap portion.

23. The system of claim 20, further comprising a second strap portion comprising a first end, a second end, and an intermediate portion extending there between, and wherein the shoulder strap portion further comprises another end operatively connected to the intermediate portion.

24. The system of claim 16, further comprising a charging unit holder adapted to receive the charging unit.

25. The system of claim 24, wherein the charging unit holder may be positioned anywhere along the shoulder strap portion.

26. The system of claim 16, wherein the antenna holder is adapted to maintain the antenna in a predetermined position within the cavity.

27. The system of claim 16, wherein the antenna holder comprises an opening to allow access to a portion of the antenna when the antenna is positioned within the cavity.

28. The system of claim 16, wherein the antenna holder comprises an opening to allow at least a portion of the antenna to be placed in proximity to a portion of the patient's body.

29. The system of claim 16, wherein the antenna holder comprises an opening adapted to receive a predetermined raised portion of the antenna.

30. A system, comprising:
an implantable device adapted to be implanted in a patient;
a charging unit;
an antenna coupled to charging unit; and
a strap comprising a shoulder strap portion, the strap adapted to be supported by a portion of the patient's body, the strap connected to a holder comprising a cavity adapted to carry the antenna to allow the antenna to transcutaneously provide energy to the implantable device.

31. The system of claim 30, wherein the strap is adapted to allow the cavity to be positionable relative to the implantable device.

* * * * *